United States Patent
Aubert et al.

(10) Patent No.: US 9,263,683 B2
(45) Date of Patent: Feb. 16, 2016

(54) USE OF COBALT COMPLEXES FOR PREPARING AN ACTIVE LAYER IN A PHOTOVOLTAIC CELL, AND CORRESPONDING PHOTOVOLTAIC CELL

(75) Inventors: Corinne Aubert, Paris (FR); Ludovic Tortech, Gif sur Yvette (FR); Vincent Gandon, Arpajon (FR); Denis Fichou, Paris (FR); Max Malacria, Paris (FR); Guillaume Bertrand, Ivry-sur-Seine (FR)

(73) Assignees: Centre National De La Recherche Scientifique, Paris (FR); Universite Pierre Et Marie Curie (Paris 6), Paris (FR)

( * ) Notice: Subject to any disclaimer, the term of this patent is extended or adjusted under 35 U.S.C. 154(b) by 195 days.

(21) Appl. No.: 14/006,523

(22) PCT Filed: Mar. 28, 2012

(86) PCT No.: PCT/FR2012/050658
§ 371 (c)(1),
(2), (4) Date: Apr. 25, 2014

(87) PCT Pub. No.: WO2012/131257
PCT Pub. Date: Oct. 4, 2012

(65) Prior Publication Data
US 2014/0290745 A1     Oct. 2, 2014

(30) Foreign Application Priority Data

Mar. 30, 2011    (FR) ...................................... 11 52641

(51) Int. Cl.
*H01L 51/00* (2006.01)
*H01L 31/072* (2012.01)
*B82Y 10/00* (2011.01)
*C07F 15/06* (2006.01)
*C07F 17/00* (2006.01)
*H01L 51/42* (2006.01)

(52) U.S. Cl.
CPC ............. *H01L 51/0083* (2013.01); *B82Y 10/00* (2013.01); *C07F 15/06* (2013.01); *C07F 17/00* (2013.01); *H01L 31/072* (2013.01); *H01L 51/0045* (2013.01); *C09K 2211/187* (2013.01); *H01L 51/0003* (2013.01); *H01L 51/0037* (2013.01); *H01L 51/0068* (2013.01); *H01L 51/0084* (2013.01); *H01L 51/424* (2013.01); *H01L 51/4253* (2013.01); *Y02E 10/549* (2013.01)

(58) Field of Classification Search
None
See application file for complete search history.

(56) References Cited

PUBLICATIONS

Byrne, et al., "Polymerization of thiophene-containing cyclobutadiene Co cyclopentadiene complexes", Synthetic Metals, vol. 156 (2006), 784-791.*

* cited by examiner

*Primary Examiner* — Jonathan Johnson
*Assistant Examiner* — William E McClain
(74) *Attorney, Agent, or Firm* — Sofer & Haroun, LLP

(57) ABSTRACT

A method for employing certain cobalt complexes as electron donors and in combination with an electron acceptor is provided for preparing an active layer in a photovoltaic conversion cell, as well as to the photovoltaic conversion cell in which the electron donor of the active layer includes such cobalt complexes.

11 Claims, 3 Drawing Sheets

USE OF COBALT COMPLEXES FOR PREPARING AN ACTIVE LAYER IN A PHOTOVOLTAIC CELL, AND CORRESPONDING PHOTOVOLTAIC CELL

RELATED APPLICATIONS

This application is a National Phase Application of PCT/FR2012/050658, filed on Mar. 28, 2012, which in turn claims the benefit of priority from French Patent Application No. 11 52641 filed on Mar. 30, 2011, the entirety of which are incorporated herein by reference.

BACKGROUND

1. Field of the Invention

The present invention relates to the use of cobalt complexes as electron donor for the preparation of an active layer (heterojunction) in a photovoltaic conversion cell, and also to the multilayer photovoltaic conversion cell having an active layer comprising at least one such cobalt complex and at least one electron acceptor.

The field of the invention may be defined as that of organic semiconductors and in particular of heterojunctions.

2. Description of Related Art

The most common photovoltaic cells consist of semiconductors, mainly based on amorphous or monocrystalline silicon (Si). They are generally in the form of thin sheets having sides of about 10 cm, sandwiched between two metal contacts, for a thickness of the order of 1 millimeter. The best-performing silicon-based cells comprise an active layer of monocrystalline silicon, the conversion efficiency of which may achieve 40% in the laboratory.

Although they have a very high-performance, photovoltaic cells based on and in particular on monocrystalline silicon, have the major drawback of being expensive due to the high cost of this raw material. This is why some research turns to cells based on thin-film semiconductors.

Specifically, the thin-film technology makes it possible to reduce the amount of semiconductors used and furthermore enables the use of substrates of low cost and large surface area. In the thin-film cells, the silicon may be amorphous silicon or crystalline, in general polycrystalline, silicon. However, photovoltaic conversion cells based on thin films made of amorphous silicon are subject to stability problems when they are exposed to the sun. Furthermore, due to its disordered structure, the charge transport properties of the amorphous silicon are mediocre, hence a mediocre efficiency. Thus, a 10-50% drop in the efficiency of these cells occurs during the first hundreds of hours of exposure to light of the cells based on amorphous silicon.

Cells based on organic semiconductors, and in particular on organometallic compounds, the cost price of which is lower than that of silicon, have already been proposed. Their use in the photovoltaic field is based on the capacity of certain π-conjugated polymers and oligomers, or else of certain π-conjugated small molecules, to convert light energy into electrical energy. When a junction is formed that is composed of two semiconductors of different natures, at least one of which is an organic compound, a heterojunction is thus defined.

Heterojunctions comprising an organic semiconductor of p type and an organic or inorganic semiconductor of n type have for several years known many applications in the field of plastic electronics and especially in the particular field of photovoltaic conversion cells. Generally, in the latter, the π-conjugated polymer or oligomers, or the π-conjugated small molecule acts as a p-type donor and is brought into contact with an n-type acceptor such as for example fullerene, or a derivative thereof. Under light irradiation, an electron-hole pair is created (exciton) on the electron donor. This exciton is dissociated by capture of the electron by the acceptor. These charges are collected at the electrodes and generate an electric current.

Many heterojunctions have thus already been proposed in the literature.

Vanlaeka et al. (Solar Energy Materials and Solar Cells, 2006, 90(14), 2150-2158) describe, for example, a heterojunction for organic photovoltaic cells, consisting of a mixture of poly(3-hexylthiophene) (P3HT) as electron donor and of methyl[6,6]-phenyl-C61-butyrate (PCBM) as electron acceptor. C. J. Brabec et al. (Synthetic Metals, 1999, 102, 861-864). F. Silvestri et al, (J. Am. Chem. Soc., 2008, 130, 17640-17641) describe the preparation of heterojunctions of photovoltaic cells from a solution of certain squaraine derivatives used as electron donors, in combination with PCBM. However, these photovoltaic cells have conversion efficiencies which are around 50% lower than those of silicon-based cells.

It has already been envisaged to use certain metallic complexes in order to improve the performances of these photovoltaic cells. It is in this way that Z. Xu et al. for example (Journal of Applied Physics, 2008, 103, 043909-1-8) indicate that the conversion performances of a heterojunction composed of a mixture of poly[2-methoxy-5-(2'-ethylhexyloxy)-1,4-phenylenevinylene] (MEH-PPV) and of PCBM can be improved by the presence of phosphorescent molecules such as $Ir(ppy)_3$ which is a complex of iridium and of tris(2-phenylpyridine). Finally, it has also already been proposed, in particular by W. K. Chan et al. (Newsroom, 2009, 10.1117/2.1200908.1757) to use, as active compound (electron donor), a heterojunction of photovoltaic devices, certain ruthenium complexes, as a mixture with a fullerene as electron acceptor. These devices do not however have a good conversion efficiency of light energy into electric current. Iridium and ruthenium are furthermore extremely rare and expensive elements.

Finally, it has already been proposed to use certain cobalt-based metallic complexes for applications in photovoltaics such as for example cobalt phthalocyanines, however these compounds have proved to be less effective than other metallic complexes such as nickel, copper or zinc complexes (Chamberlain, G. A., Solar Cells, 1983, 8, 47-83).

OBJECTS AND SUMMARY

There is therefore a need for compounds that have a cost price lower than that of silicon and that can in particular be used as electron donor for the preparation of an active layer in a photovoltaic conversion cell.

The inventors have now discovered that certain cobalt complexes, the formula of which will be defined below, have excellent electron donor properties, which enables them to advantageously be used, in combination with an electron acceptor, for the preparation of an active layer (heterojunction) in a photovoltaic conversion cell.

One subject the present invention is the use of at least one cobalt complex of formula (I-a) or (I-b) below:

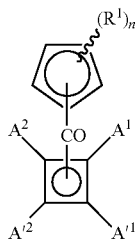
(I-a)

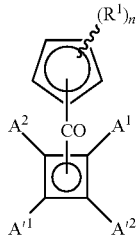
(I-b)

wherein:

n is an integer that varies from 0 to 5;

$R^1$ is chosen from I, $C_1$-$C_{12}$ alkyl, trimethylsilyl, HgCl, —C(O)($C_1$-$C_4$)alkyl, and an oxazole group optionally substituted by a $C_1$-$C_4$ alkyl radical, it being understood that when n>1, all the $R^1$ radicals of a given compound of formula (I-a) or (I-b) are identical, the groups $A^1$, $A'^1$, $A^2$ and $A'^2$ are identical in pairs and are chosen from the groups of formulae (II-1) to (II-9) below:

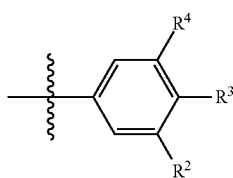
(II-1)

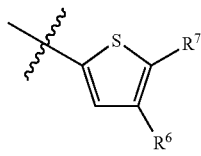
(II-2)

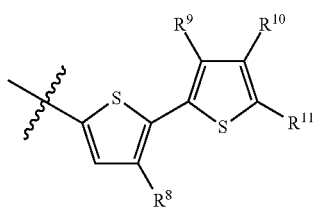
(II-3)

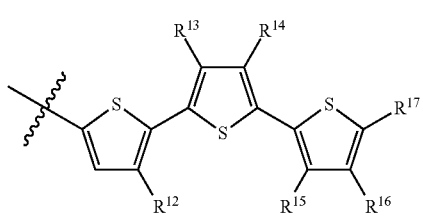
(II-4)

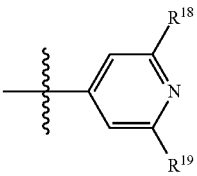
(II-5)

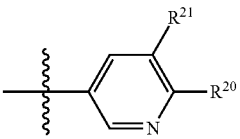
(II-6)

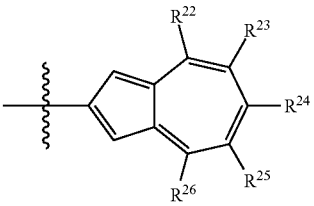
(II-7)

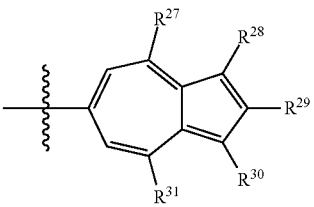
(II-8)

and

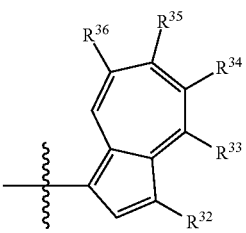
(II-9)

wherein:

$R^2$, $R^3$, and $R^4$, which are identical or different, represent a hydrogen, iodine or bromine atom, a nitro, linear $C_1$-$C_{12}$ alkyl, trifluoromethyl, di($C_1$-$C_4$)alkylamino, —C(O)($C_1$-$C_4$)alkyl or linear $C_1$-$C_4$ alkoxy radical;

$R^6$, $R^8$, $R^9$, $R^{10}$, $R^{12}$, $R^{13}$, $R^{14}$, $R^{15}$ and $R^{16}$, which are identical or different, represent a hydrogen or bromine atom, a linear $C_1$-$C_{12}$ alkyl or linear $C_1$-$C_4$ alkoxy radical, $R^9$ and $R^{10}$ together and/or $R^{13}$ and $R^{14}$ together and/or $R^{15}$ and $R^{16}$ together may also form an ethylenedioxy group (—O—($CH_2$)$_2$—O—);

$R^7$, $R^{11}$ and $R^{17}$ represent a hydrogen, bromine or iodine atom, a nitro, linear $C_1$-$C_{12}$ alkyl, linear $C_1$-$C_4$ alkoxy, —CHO, —C(O)($C_1$-$C_4$)alkyl or —C(O)($C_1$-$C_4$)alkoxy radical or a thiophene ring optionally bearing one or more substituents chosen from Br, I, nitro, linear $C_1$-$C_{12}$ alkyl, linear $C_1$-$C_4$ alkoxy, —C(O)($C_1$-$C_4$)alkyl and —C(O)($C_1$-$C_4$)alkoxy;

$R^{18}$ to $R^{36}$, which are identical or different, represent a hydrogen atom, a linear $C_1$-$C_4$ alkoxy radical, a nitro radical or a —C(O)($C_1$-$C_4$)alkoxy radical, as an electron donor and in combination with an electron acceptor, for the preparation of an active layer (heterojunction) in a photovoltaic conversion cell.

The compounds of formulae (I-a) and (I-b) defined above are readily accessible, and in combination with an n-type semiconductor compound, such as for example methyl[6,6]-phenyl-C61-butyrate (PCBM) or other, they can be deposited as a wet layer and prove to be very good p-type conductors.

According to invention, the expression "$A^1$, $A'^1$, $A^2$ and $A'^2$ are identical in pairs" used for characterizing the $A^1$, $A'^1$, $A^2$ and $A'^2$ groups, means that in each of the compounds of formulae (I-a) and (I-b), $A^1=A'^1$, $A^2=A'^2$, and $A^1$ ($A'^1$) is identical to or different from $A^2$ ($A'^2$).

Among the $C_1$-$C_{12}$ alkyl radicals mentioned for the $R^1$ to $R^{17}$ radicals, mention may more particularly be made of the methyl, ethyl, n-propyl, n-butyl, n-pentyl and n-hexyl radicals. Among these radicals, the methyl and n-hexyl radicals are preferred.

Among the $C_1$-$C_4$ alkoxy radicals mentioned for the $R^1$ to $R^{21}$ radicals, the methoxy radical is preferred.

According to one preferred embodiment of the invention, n is equal to 1 or 2, and the $R_1$ radical(s) represent(s) a methyl radical.

Among the complexes of formulae (I-a) and (I-b) above, mention may in particular be made of:

[1,1',1",1'''-(η4-1,3-cyclobutadiene-1,2,3,4-tetrayl)tetrakis [benzene]](η5-cyclopentadienyl)cobalt(I);

[1,1',1",1'''-(η4-1,3-cyclobutadiene-1,2,3,4-tetrayl)tetrakis-4-n-butyl-benzene]](η5-cyclopentadienyl)cobalt(I);

[1,1',1",1'''-(η4-1,3-cyclobutadiene-1,2,3,4-tetrayl)tetrakis [3,5-dimethoxy-benzene]](η5-cyclopentadienyl)cobalt (I);

[1,1'-[(1,2,3,4-η)-2,4-bis(4-methoxybenzene)-1,3-cyclobutadien-1,3-diyl]-bis[phenyl]](η5-2,4-cyclopentadien-1-yl)cobalt(I);

[1,1'-[(1,2,3,4-η)-2,4-bis(4-nitrobenzene)-1,3-cyclobutadien-1,3-diyl]bis-[phenyl]](η5-2,4-cyclopentadien-1-yl) cobalt(I);

[1,1'-[(1,2,3,4-η)-2,4-bis(4-nitrobenzene)-1,3-cyclobutadien-1,3-diyl]bis[4-methoxybenzene]](η5-2,4-cyclopentadien-1-yl)cobalt(I);

[1,1'-[(1,2,3,4-η)-2,4-bis(4-bromobenzene)-1,3-cyclobutadien-1,3-diyl]bis-[4-methoxybenzene]](η5-2,4-cyclopentadien-1-yl)cobalt(I);

[1,1',1",1'''-(η4-1,3-cyclobutadiene-1,2,3,4-tetrayl)tetrakis [4-methyl benzoate]](η5-cyclopentadienyl)cobalt(I);

[1,1',1",1'''-(η4-1,3-cyclobutadiene-1,2,3,4-tetrayl)tetrakis [2,2',5'-bithiophene]](η5-cyclopentadienyl)cobalt(I);

[1,1',1",1'''-(η4-1,3-cyclobutadiene-1,2,3,4-tetrayl)tetrakis [2,2',5',2",5"-terthiophene]](η5-cyclopentadienyl)cobalt (I);

[1,1',1",1'''-(η4-cyclobutadiene-tetrakis 1,2,3,4-[2,5,2',5',2"-terthiophene-5"-carbaldehyde])]-(η5-cyclopentadienyl) cobalt(I);

[1,1',1",1'''-(η4-cyclobutadiene-tetrakis 1,2,3,4-[2,5,2',5',2"-terthiophene-5"-bromo])](η5-cyclopentadienyl)cobalt(I);

1,1',1",1'''-(η4-cyclobutadiene-tetrakis 1,2,3,4-[2,5,2',5',2"-terthiophene-5"-methoxy])](η5-cyclopentadienyl)cobalt (I);

[1,1',1",1'''-(η4-cyclobutadiene-tetrakis 1,2,3,4-[2,5,2',5',2"-terthiophene-5"-nitro])](η5-cyclopentadienyl)cobalt(I);

[1,1',1",1'''-(η4-cyclobutadiene-tetrakis 1,2,3,4-[2,5,2',5',2"-terthiophene-(4,4',4")-trishexyl])](η5-cyclopentadienyl) cobalt(I);

[1,1',1",1'''-(η4-cyclobutadiene-tetrakis 1,2,3,4-[2,5,2',5',2"-terthiophene-5"-dodecyl])](η5-cyclopentadienyl)cobalt (I);

[1,1',1",1'''-(η4-cyclobutadiene-tetrakis 1,2,3,4-[2,5,2',5',2"-terthiophene-5"-iodo])](η5-cyclopentadienyl)cobalt(I);

[1,1',1",1'''-(η4-cyclobutadiene-bis 1,3-[2,5,2',5',2"-terthiophene-5"-nitro], bis 2,4-[2,5,2',5',2"-terthiophene-5"-methoxy])](η5-cyclopentadienyl)-cobalt(I);

[1,1',1",1'''-(η4-cyclobutadiene-bis 1,3-[2,5,2',5',2"-terthiophene-5"-bromo], bis 2,4-[2,5,2',5',2"-terthiophene-5"-methoxy])](η5-cyclopenta-dienyl)cobalt(I);

[1,1',1",1'''-(η4-1,3-cyclobutadiene-1,2,3,4-tetrayl)tetrakis [2-thionyl]](η5-cyclopentadienyl)cobalt(I);

[1,1',1",1'''-(η4-1,3-cyclobutadiene-1,2,3,4-tetrayl)tetrakis [3-pyridyl]](η5-cyclopentadienyl)cobalt(I);

[1,1',1",1'''-(η4-1,3-cyclobutadiene-1,2,3,4-tetrayl)tetrakis [4-pyridyl]](η5-cyclopentadienyl)cobalt(I);

[1,1',1",1'''-(η4-1,3-cyclobutadiene-1,2,3,4-tetrayl)tetrakis [1-azulenyl]](η5-cyclopentadienyl)cobalt(I);

[1,1',1",1'''-(η4-1,3-cyclobutadiene-1,2,3,4-tetrayl)tetrakis [2-azulenyl]](η5-cyclopentadienyl)cobalt(I); and

[1,1',1",1'''-(η4-1,3-cyclobutadiene-1,2,3,4-tetrayl)tetrakis [6-azulenyl]](η5-cyclopentadienyl)cobalt(I).

Among these compounds, the following are very particularly preferred:

[1,1',1",1'''-(η4-1,3-cyclobutadiene-1,2,3,4-tetrayl)tetrakis [2,2',5'-bithiophene]](η5-cyclopentadienyl)cobalt(I);

[1,1',1",1'''-(η4-1,3-cyclobutadiene-1,2,3,4-tetrayl)tetrakis [2,2',5',2",5"-terthiophene]](η5-cyclopentadienyl)cobalt (I);

[1,1',1",1'''-(η4-cyclobutadiene-tetrakis 1,2,3,4-[2,5,2',5',2"-terthiophene-5"-carbaldehyde])](η5-cyclopentadienyl) cobalt(I);

[1,1',1",1'''-(η4-cyclobutadiene-tetrakis 1,2,3,4-[2,5,2',5',2"-terthiophene-5"-bromo])](η5-cyclopentadienyl)cobalt(I);

[1,1',1",1'''-(η4-cyclobutadiene-tetrakis 1,2,3,4-[2,5,2',5',2"-terthiophene-5"-methoxy])](η5-cyclopentadienyl)cobalt (I);

[1,1',1",1'''-(η4-cyclobutadiene-tetrakis 1,2,3,4-[2,5,2',5',2"-terthiophene-5"-nitro])](η5-cyclopentadienyl)cobalt(I);

[1,1',1",1'''-(η4-cyclobutadiene-tetrakis 1,2,3,4-[2,5,2',5',2"-terthiophene-(4,4',4")-trishexyl])](η5-cyclopentadienyl) cobalt(I);

[1,1',1",1'''-(η4-cyclobutadiene-tetrakis 1,2,3,4-[2,5,2',5',2"-terthiophene-5"-dodecyl])](η5-cyclopentadienyl)cobalt (I);

[1,1',1",1'''-(η4-cyclobutadiene-tetrakis 1,2,3,4-[2,5,2',5',2"-terthiophene-5"-iodo])](η5-cyclopentadienyl)cobalt(I);

[1,1',1",1'''-(η4-cyclobutadiene-bis 1,3-[2,5,2',5',2"-terthiophene-5"-nitro], bis 2,4-[2,5,2',5',2"-terthiophene-5"-methoxy])](η5-cyclopentadienyl)-cobalt(I); and

[1,1',1",1'''-(η4-cyclobutadiene-bis 1,3-[2,5,2',5',2"-terthiophene-5"-bromo], bis 2,4-[2,5,2',5',2"-terthiophene-5"-methoxy])](η5-cyclopenta-dienyl)cobalt(I).

The compounds of formulae (I-a) and (I-b) as defined above, when they are not commercially available, may be prepared according to a simple and inexpensive process, comprising the following steps:

a) the preparation of a group of formula (III) below:

(III)

by Sonogashira coupling between an $A^1$-Br group and an $A^2$-Br group, which may be identical or different, and both chosen from one of the groups of formulae (IV-1) to (IV-9) below:

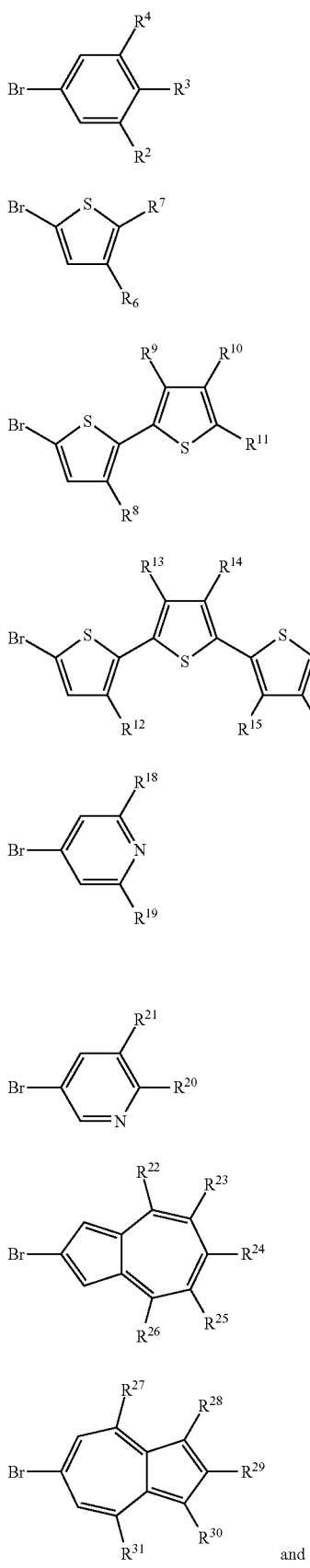

(IV-1)
(IV-2)
(IV-3)
(IV-4)
(IV-5)
(IV-6)
(IV-7)
(IV-8)

and

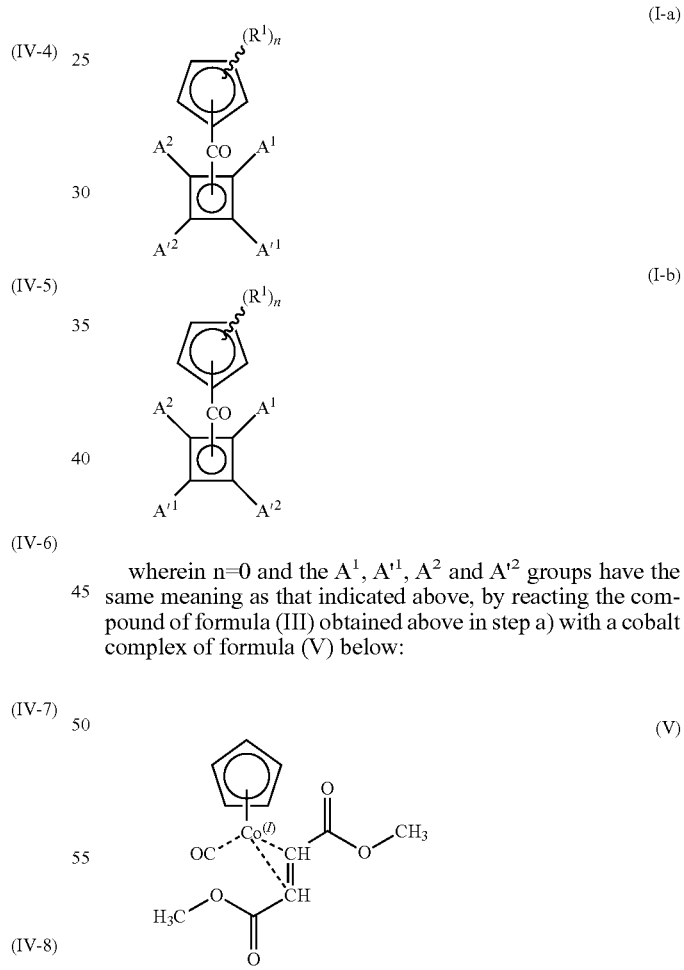

(IV-9)

wherein the $R^2$ to $R^{36}$ radicals have the same meaning as that indicated above for the groups of formulae (II-1) to (II-9); said coupling being carried out in an organic solvent of amine type, in the presence of trimethylsilylethyne (TMSA), of an organic base or an alkali metal salt in solution in an organic solvent, of a palladium complex as catalyst and of a copper(I) salt as co-catalyst;

b) the preparation of a compound of formula (I-a) or of formula (I-b) below:

(I-a)

(I-b)

wherein n=0 and the $A^1$, $A'^1$, $A^2$ and $A'^2$ groups have the same meaning as that indicated above, by reacting the compound of formula (III) obtained above in step a) with a cobalt complex of formula (V) below:

(V)

in an organic solvent, at a temperature of 145° C. to 150° C., said reaction being carried out in the presence of microwaves having a power of from 60 to 120 W for a duration of between 30 min to 1 hour; then, when it is desired to obtain a compound of formula (I-a) or (I-b) wherein n≠0, c) the functionalization of the compounds of formulae (I-a) and (I-b) by one of more $R^1$ radicals, by reacting the compound of formula (I-a) or (I-b) wherein n=0 obtained above in step b), with a compound of formula (VI) below:

R¹—X   (VI)

wherein:

R¹ is chosen from $C_1$-$C_{12}$ alkyl, $C_1$-$C_4$ alkoxy, trimethylsilyl, C(O)($C_1$-$C_4$)alkyl, phosphane, and an oxazole group optionally substituted by a $C_1$-$C_4$ alkyl radical, and X represents a halogen atom chosen from chlorine and iodine, it being understood that when X=Cl, $R_1$ may also represent an HgCl group, and when X=I, $R_1$ may also denote an iodine atom;

said functionalization being carried out in a solvent and in the presence of an acid and of a mercury salt as catalyst, of lithium chloride and of n-butyllithium, in order to obtain a compound of formula (I-a) or (I-b) wherein n≠0.

This process is simple and inexpensive to implement, and it makes it possible to attain compounds of formulae (I-a) and (I-b) with a very good yield.

Furthermore, use of microwaves during step b) makes it possible to limit the formation of byproducts and increase the reactivity of the starting products. The desired product is thus obtained with a greater yield, in less time and more cleanly.

The amine-type solvent used during the Sonogashira coupling reaction (Sonogashira K. et al., Tetrahedron Letters, 1975, 4467) of step a) for the preparation of the groups of formula (III), can be chosen from triethylamine and diethylamine.

When an alkali metal salt is used during step a), this is preferably potassium carbonate, in solution in a solvent mixture consisting of tetrahydrofuran and methanol.

When an organic base is used during step a), this may especially be chosen from 1,8-diazabicyclo[5,4,0]undec-7-ene (DBU) and potassium tert-butanolate.

The palladium complex used as catalyst during step a) is preferably bis(triphenylphosphine)palladium(II) dichloride (Pd(Cl)$_2$(PPh$_3$)$_2$ and the copper salt used as co-catalyst, cupric iodide.

The duration of step a) generally varies from 1 to 12 hours approximately.

The A¹-Br and A²-Br groups of formulae (IV-1) to (IV-9), used during step a), when they are not commercially available, may be prepared, prior to step a), according to processes well known from the prior art and as described for example in the following publications:

M. Lamberto et al. Tetrahedron Letters, 2005, 46(29), 4895-4899;

S. Ito et al, J. Org. Chem., 2002, 67(21), 7295-7302;

S. Ito et al, Tetrahedron Letters, 2004, 45(14), 2891-2894;

K. M. Maloney, et al, Journal of Organic Chemistry, 2009, 74(14), 5111-5114.

By way of example, the groups of formula (IV-4) may be synthesized according to a process that consists in reacting, in an organic solvent, and in the presence of a catalyst, potassium carbonate and N-bromosuccinimide:

i) a compound of formula (VII) below:

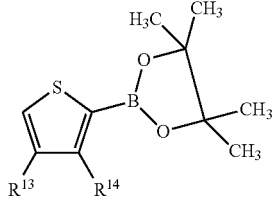

with a bromothiophene of formula (VIII) below:

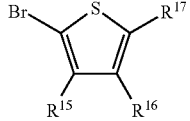

in order to obtain a compound of formula (IX) below:

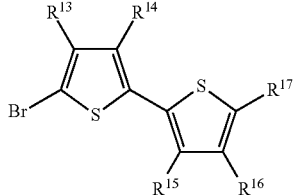

in which formulae (VII), (VIII) and (IX) the $R^{13}$, $R^{14}$, $R^{15}$, $R^{16}$ and $R^{17}$ radicals have the same meaning as that indicated above for the groups of formula (II-4), then ii) the compound of formula (IX) obtained above in step i) with a compound of formula (X) below:

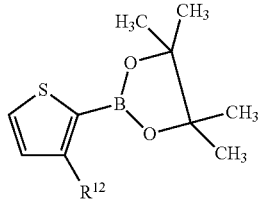

wherein the $R^{12}$ radical has the same meaning as that indicated above for the groups of formula (II-4), in order to obtain the expected group of formula (IV-4).

The organic solvent used in the preparation of the A¹-Br or A²-Br groups may be chosen from tetrahydrofuran (THF) and diethyl ether.

The compounds of formulae (VII), (VIII) and (IX) above, when they are not commercially available, can be prepared according to methods well known to a person skilled in the art and as described for example in the following publications:

J. B. Press et al., J. Org. Chem., 1979, 44(19), 3293;

S. Kawamorita et al., J. Org. Chem., 2010, 75(11), 3855-3858;

S. W. Hell et al., Angew. Chem. Int. Ed., 2006, 45, 7462-7465;
A. H. M. Elwahy, et al, Euro. J. Org. Chem., 2010, 2, 265-27;
A. H. M. Elwahy, et al, Tetrahedron Letters, 2000, 41(16), 2859-2862;
E. M. Harcourt, et al, Organometallics, 2008, 27(7), 1653-1656; and
U. S. Sorensen, and E. Pombo-Villar, Tetrahedron, 2005, 61(10), 2697-2703.

The catalyst used in the preparation of the $A^1$-Br or $A^2$-Br groups is preferably chosen from palladium catalysts such as for example tetrakis(triphenylphosphine)palladium, palladium diacetate and bis(triphenylphosphine)palladium chloride.

The organic solvent used during step b) of preparing compounds of formula (I-a) or (I-b) wherein n=0 is preferably chosen from ethanol, dimethylformamide (DMF), tetrahydrofuran (THF), the THF (95% by volume)/ethanol (5% by volume) mixture, pyridine, the dichloromethane (95% by volume)/ethanol (5% by volume) mixture, the xylene (95% by volume)/ethanol (5% by volume) mixture and the toluene (95% by volume)/ethanol (5% by volume) mixture. These solvents are classed in order of the lowest to highest microwave powers that are needed to carry out the reaction of step b).

Thus, the power of the microwaves applied during step b) can be adjusted as a function of the nature of the solvent used. For example, the lowest powers (close to 60 W) can be used when the solvent is ethanol or DMF, whereas the highest powers (of the order of 120 W approximately) are preferred when the solvent is a xylene (95% by volume)/ethanol (5% by volume) mixture or a toluene (95% by volume)/ethanol (5% by volume) mixture.

The solvent used in step c) of functionalizing the compounds of formulae (I-a) and (I-b), wherein n=0, with one or more $R^1$ radicals, is preferably tetrahydrofuran or dioxane.

Among the acids that can be used during step c), mention may especially be made of perhydrochloric acid.

Among the mercury salts that can be used during step c), mention may especially be made of mercury acetate, and mercury dichloride.

During step c), the number of $R^1$ radicals substituting the pentadienyl ring of the compounds of formula (I-a) or (I-b), that is to say the value of n, can be chosen by adjusting the number of equivalents of mercury salt and of alkyllithium.

This process is simple, reproducible and inexpensive to implement and results in complexes of formula (I-a) or (I-b) being obtained with a yield of the order of 65% to 95%.

Between each of the synthesis steps, the intermediate compounds are preferably purified by any appropriate technique known to a person skilled in the art, for example by passing through a chromatography column.

As was seen above, the complexes of formulae (I-a) and (I-b) are very good semiconductors and can thus be used as electron donor for the preparation of a heterojunction of a photovoltaic conversion cell.

Another subject of the invention is therefore a photovoltaic conversion cell comprising at least one support, a positive electrode, an active layer (heterojunction) comprising at least one electron donor and at least one electron acceptor, and a negative electrode, said cell being characterized in that the electron donor is chosen from the compounds of formulae (I-a) and (I-b) as defined above.

The electron acceptor is preferably chosen from fullerene (C60, C70) derivatives, such as methyl[6.6]-phenyl-C61-butyrate (PCBM), carbon nanotubes, perylene derivatives and tetracyanoquinodimethane (TCNQ) derivatives.

According to one preferred embodiment, the compound of formula (I-a) or (I-b)/electron acceptor weight ratio varies from 2/1 to 1/4.

According to the invention, the substrate is preferably a transparent substrate made of a material which may be flexible or rigid, for example glass, and deposited on which is a positive electrode, consisting of an oxide of metals, for example indium tin oxide (ITO).

The negative electrode is preferably an aluminum electrode.

According to one preferred embodiment of the invention, a buffer layer is inserted between the active layer and the positive electrode in order to improve the interface between these two layers. Such a buffer layer may especially consist of a layer of a mixture of two polymers: poly(3,4-ethylenedioxythiophene) (PEDOT) and poly(sodium styrenesulfonate) (PSS):PEDOT:PSS layer.

Equally preferably, a buffer layer is also inserted between the active layer and the negative electrode in order to improve, here too, the interface between these two layers. Such a buffer layer may especially consist of a layer of lithium fluoride (LiF).

The photovoltaic cell in accordance with the invention may be prepared according to the techniques known to a person skilled in the art, and especially according to a process that consists in depositing, on a positive electrode previously covered with a buffer layer, a solution of at least one compound of formula (I) and of at least one electron acceptor in an appropriate solvent such as for example dichlorobenzene. The deposition of the active layer may be carried out by any appropriate technique, and preferably by spin coating.

The deposition of a second buffer layer on the active layer, then of the negative electrode, can also be carried out by any appropriate technique known to a person skilled in the art, and in particular by vapor deposition.

The present invention is illustrated by the following exemplary embodiments, to which it is not however limited.

DETAILED DESCRIPTION

Examples

Figure 1:
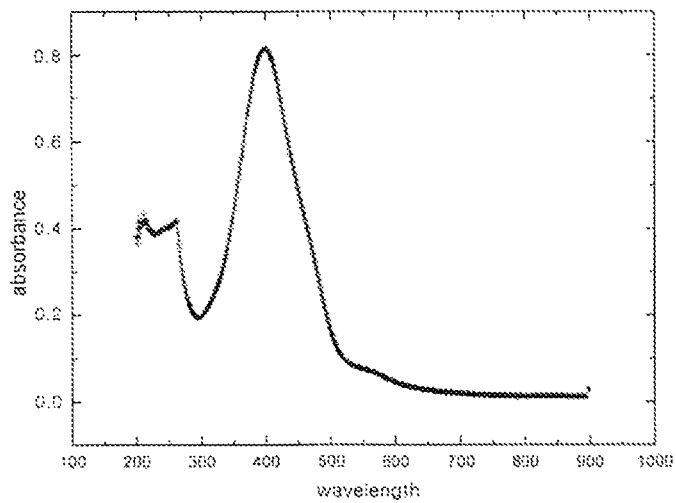
FIG. 1 is an absorbance graph from Example 1, in accordance with one embodiment.

The following raw materials were used in the examples:
2,2':5',2''-terthiophene; 2-(carboxaldehyde)-(5,2'-bithiophene); and 2-iodo-(5,2'-bithiophene) sold by the company TCI Chemicals;
methanol; N-iodosuccinimide; benzene; diazabicyclo[5,4,0]undec-7-ene (DBU); butyllithium; hexane; 4-methoxyiodobenzene; 4-nitroiodobenzene; and 4-iodobenzoic acid methyl ester sold by the company Sigma Aldrich;
petroleum ether; dichloromethane; toluene; ethanol; tetrahydrofuran (THF); and triphenylphosphine sold by the company VWR;

bis(triphenylphosphine)palladium(II) chloride; trimethylsilylacetylene (TMSA); bis(benzene)acetylene; tetrabromomethane; 3,5-dimethoxybenzaldehyde; 3,5-dimethoxyiodobenzene; ethynylbenzene; and tetrabromomethane sold by the company Acros;

cupric iodide (CuI); and biscarbonylcyclopentadienyl cobalt (I), sold by the company Strem;

dimethyl fumarate; and bis[4-n-butylbenzene]acetylene sold by the company Alfa Aezer;

PEDOT:PSS: poly(3,4-ethylenedioxythiophene):poly (styrenesulfonate) sold by the company Sigma Aldrich;

PCBM: methyl[6,6]-phenyl-C61-butyrate sold by the company Sigma Aldrich.

Example 1

1) Synthesis of [1,1',1'',1'''-(η4-cyclobutadiene-1,2,3,4-tetrayl)tetrakis[2,2':5',2'',5''-terthiophene]](η5-cyclopentadienyl)cobalt(I)

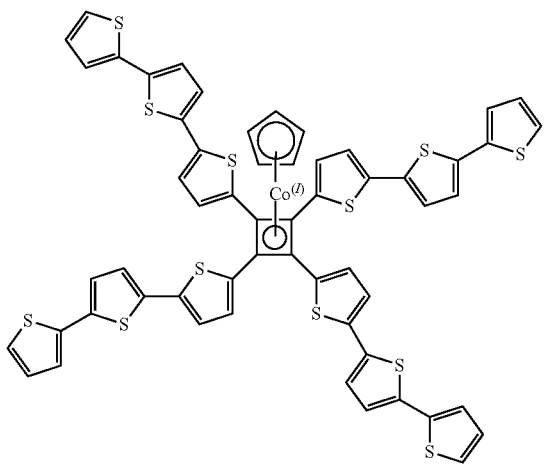

1) First Step: Synthesis of 2-iodo(5,2':5',2''-terthiophene)

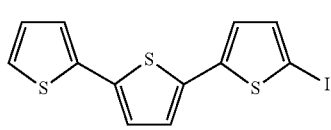

(1)

500 mg (2.02 mmol) of the commercial product (2,2':5',2''-terthiophene) were diluted in 100 ml of methanol at 0° C. 1.1 equivalents of N-iodosuccinimide (NIS, 546 mg, 2.1 mmol) were then added. The mixture was left stirring, in the dark for 12 h. The solvent was then evaporated under reduced pressure. The crude product of the reaction was then purified by column chromatography using, as eluent, petroleum ether then a petroleum ether/dichloromethane (5/1: v/v) mixture.

The expected product was isolated in the form of a yellow powder (285 mg; yield=45%).

2) Second Step: Synthesis of bis(2,2':5',2''-terthiophene)acetylene

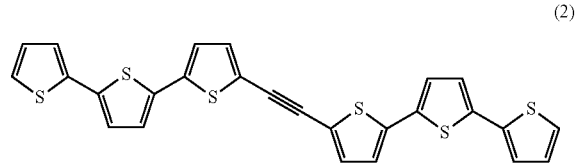 [SMILES: C(#Cc1ccc(-c2ccc(-c3cccs3)s2)s1)c1ccc(-c2ccc(-c3cccs3)s2)s1]

(2)

150 mg (0.4 mmol) of 2-iodo(5,2':5',2''-terthiophene) obtained above in the preceding step were introduced into a round-bottomed flask along with 9 mg of bis(triphenylphosphine)palladium(II) chloride $(Pd(Cl_2)(PPh_3)_2)$ (24 μmol) and 8 mg of CuI (40 μmol). The round-bottomed flask was purged 3 times (vacuum/argon). 50 ml of distilled benzene, 0.8 ml of DBU (7 equivalents, 2.8 mmol), 29 μl of TMSA (0.5 equivalent, 0.2 mmol) and 3 μl of distilled water (0.4 eq., 0.16 mmol) were added in this order to the reaction medium. The mixture was left stirring for 24 h in the dark at ambient temperature. The solvent was then evaporated under reduced pressure, then the crude product was purified by passing through a chromatographic column (eluent: petroleum ether, 1 L/dichloromethane, 3 L). The product was isolated in the form of a dark brown powder (82 mg, yield: 32%). This compound was directly inserted into the reaction described below in the fourth step.

3) Third Step: Synthesis of (η2-dimethyl fumarate)carbonyl(η5-cyclopenta-dienyl)cobalt (I)

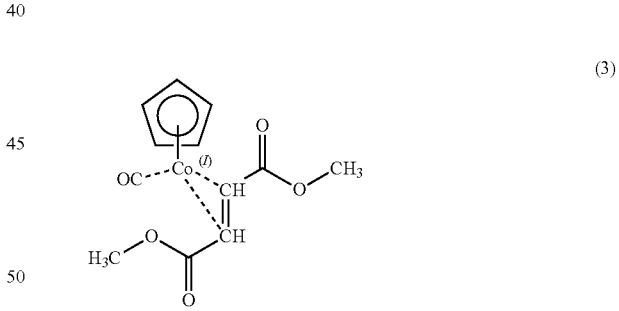

(3)

1.44 g (10 mmol) of dimethyl fumarate were dissolved in 150 ml of distilled toluene contained in a round-bottomed flask. The round-bottomed flask was then purged 3 times with argon. Next, 1.4 ml (10 mmol) of biscarbonylcyclopentadienyl cobalt (I) were added and the reaction mixture was stirred under toluene reflux and under irradiation (simple halogen lamp) for a time of 6 h. The solvent was evaporated under reduced pressure. The crude product of the reaction was then purified by column chromatography: (eluent: 3:1 (v/v) petroleum ether/ethyl acetate). The product was then isolated in the form of a red powder (m=1.98 mg, yield: 66%):

$^1$H NMR (400 MHz, CDCl$_3$) δ 3.28 (d, J=10.3 Hz, 1H); 3.61 (s, 3H); 3.71 (s, 3H); 3.86 (d, J=10.3 Hz, 1H); 4.99 (s, 5H).

$^{13}$C NMR (101 MHz, CDCl$_3$) δ 37.1; 38.2; 51.4; 51.5; 87.2; 175.6; 176.2; 199.2. This spectrum is in agreement with those from the literature: A. Geny, et al., Ang. Chem. Int. Ed., 2009, 48(10), 1810-1813.

4) Fourth Step: Synthesis of [1,1',1'',1'''-(η4-cyclobutadiene-1,2,3,4-tetrayl)tetrakis[2,2',5',2'',5''-terthiophene]](η5-cyclopentadienyl)cobalt(I)

In a sealed tube, 42 mg (2 eq., 82 μmol) of bis(2,2':5',2''-terthiophene)acetylene obtained above in the second step and 18 mg of (η2-dimethyl fumarate)carbonyl(η5-cyclopentadienyl)cobalt (I) (1.5 equivalents, 61 μmol) were diluted in 1 ml of ethanol and 14 ml of THF. The reaction medium was then heated at 150° C. using a microwave (90 watts, stationary regime) for 45 min. The solvents were then evaporated under reduced pressure, and then the crude product was filtered with ethanol (25 ml). The resulting cake was filtered with dichloromethane, to give the expected product in the form of a black powder (25 mg, yield: 45%).

$^1$H NMR (400 MHz, CDCl$_3$) δ 7.23 (d, J=5.1; 4H); 7.19 (d, J=3.6; 8H); 7.10 (dd, J=3.7; 8.9; 8H); 7.05-7.00 (m, 8H); 4.86 (s, 5H).

$^{13}$C NMR (101 MHz, CDCl$_3$) δ 137.30; 137.04; 136.74; 136.33; 136.26; 128.11; 128.08; 124.64; 124.60; 124.33; 124.11; 123.83; 84.02; 69.68.

The absorption spectrum of the compound (1) was measured with a UV-visible spectrophotometer sold by the company Perkin Elmer under the reference Lambda 650, in solution at 0.1 mg/ml (85 μmol/L) in dichloromethane. It is reported in appended FIG. 1, in which the absorbance in arbitrary units is a function of the wavelength in nm ($\lambda_{max}$=399 nm; ε=9.3×10$^4$ cm$^{-1}$·L·mol$^{-1}$; Egap=1.9 eV).

Example 2

Synthesis of [1,1',1'',1'''-(η4-cyclobutadiene-tetrakis 1,2,3,4-[2,5,2',5',2''-terthiophene-5''-carbaldehyde])] (η5-cyclopentadienyl)cobalt(I)

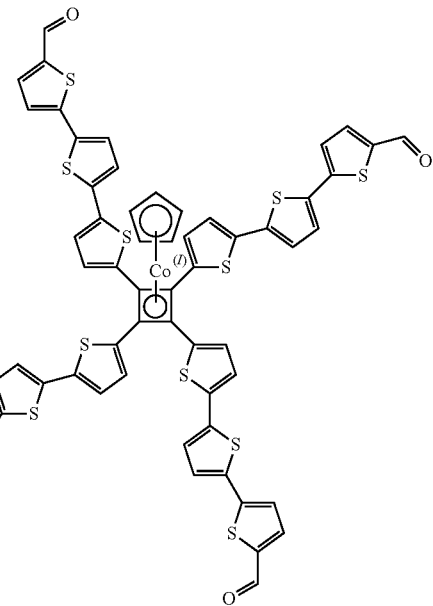

The 2-bromo-(2,2':5',2''-terthiophene-5''-carbaldehyde) of formula below was available commercially from TCI Chemicals:

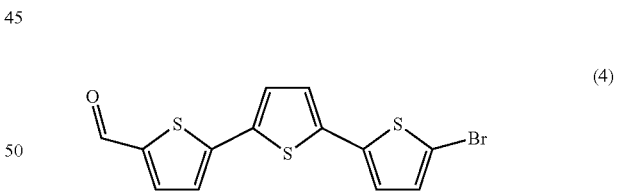

(4)

2) First Step: Synthesis of bis(2,2':5',2''-terthiophene-5''-carbaldehyde)-acetylene

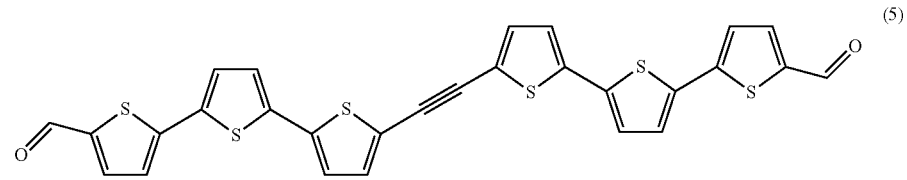 [SMILES: O=Cc1ccc(-c2ccc(-c3ccc(C#Cc4ccc(-c5ccc(-c6ccc(C=O)s6)s5)s4)s3)s2)s1]

(5)

120 mg (0.34 mmol) of 2-bromo-(2,2':5',2"-terthiophene-5"-carbaldehyde) (4) (TCI Chemicals), 10 mg of bis(triphenylphosphine)palladium(II) chloride (Pd(Cl$_2$)(PPh$_3$)$_2$) (30 µmol) and 8 mg of CuI (40 µmol) were introduced into a round-bottomed flask. The round-bottomed flask was then purged 3 times (vacuum/argon). 50 ml of distilled benzene, 0.75 ml of DBU (7 equivalents, 2.4 mmol), 23 µl of TMSA (0.5 equivalent, 0.16 mmol) and 3 µl of distilled water (0.4) were then added in this order to the reaction medium. The mixture was left stirring for 24 h in the dark at ambient temperature. The solvent was then evaporated under reduced pressure, then the crude product was purified by passing through a chromatographic column (eluent: dichloromethane 5 L). The expected product was isolated in the form of a dark brown powder (36 mg, yield: 39%). This compound was directly inserted into the reaction described below.

3) Second Step: Synthesis of [1,1',1",1'''-(η4-cyclobutadiene-tetrakis 1,2,3,4-[2,5,2',5',2"-terthiophene-5"-carbaldehyde])](η5-cyclopentadienyl)cobalt(I)

In a sealed tube, 36 mg (2 eq., 62 µmol) of bis(2,2':5',2"-terthiophene-5"-carbaldehyde)acetylene obtained above in the first step and 14 mg of (η2-dimethyl fumarate)carbonyl (η5-cyclopentadienyl)cobalt (I) (1.5 equivalents, 45 µmol) were diluted in 1 ml of ethanol and 14 ml of THF. The reaction medium was then heated at 150° C. using a microwave (90 watts, stationary regime) for 45 min. The solvents were then evaporated under reduced pressure, and then the crude product was filtered with ethanol (25 ml). The resulting cake was filtered with dichloromethane, to give the expected product in the form of a black powder (10 mg, yield: 26%).

$^1$H NMR (400 MHz, CDCl$_3$) δ 9.06 (s, 4H) 7.36 (d, J=5.8; 4H); 7.29 (d, J=3.5; 8H); 7.15 (dd, J=3.5; 8.6; 8H); 7.09-7.00 (m, 8H); 4.91 (s, 5H).

$^{13}$C NMR (101 MHz, CDCl$_3$) δ 187.90; 148.11; 139.01; 137.21; 137.00; 136.87; 129.38; 128.98; 126.66; 126.49; 125.92; 125.61; 124.73; 86.86; 70.00.

Example 3

Synthesis of [1,1',1",1'''-(η4-cyclobutadiene-tetrakis 1,2,3,4-[2,5,2',5',2"-terthiophene-5"-bromo])](η5-cyclopentadienyl)cobalt(I)

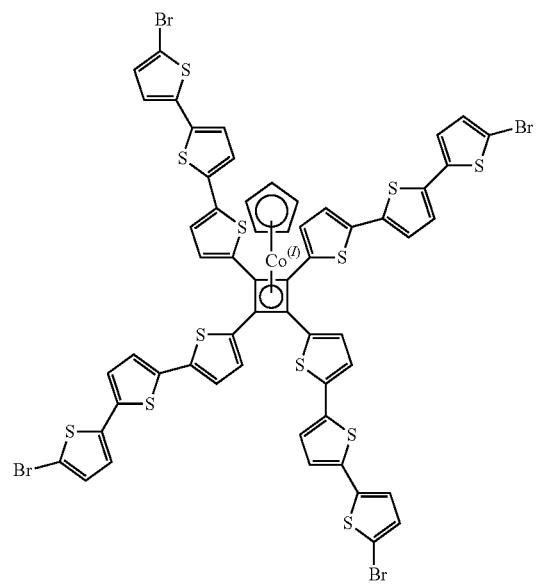

1) First Step: Synthesis of 2-iodo-5"-bromo(5,2':5', 2"-terthiophene) (Compound no. 5)

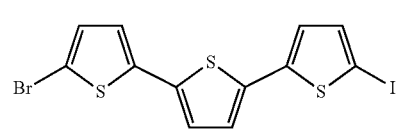

(5)

100 mg (0.27 mmol) of 2-iodo(5,2':5',2"-terthiophene) (1) obtained above in the first step of example 1 were diluted in 100 ml of methanol at 0° C. 2 equivalents of N-bromosuccinimide (NBS, 95 mg, 0.53 mmol) were then added. The mixture was left stirring, in the dark for 12 h. The solvent was then evaporated under reduced pressure. The crude product of the reaction was then purified by column chromatography using, as eluent, petroleum ether then a petroleum ether/dichloromethane (5/1: v/v) mixture. The expected product was isolated in the form of a yellow powder (115 mg; yield=95%).

2) Second Step: Synthesis of bis(2,2':5',2"-terthiophene-5"-bromo)acetylene (Compound 6)

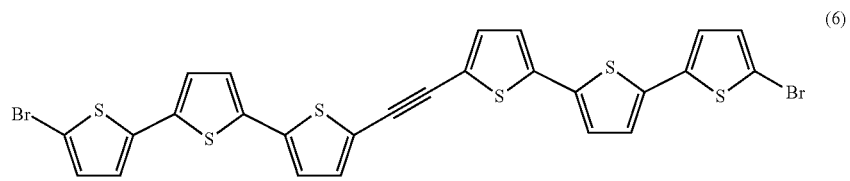 [SMILES: Brc1ccc(-c2ccc(-c3ccc(C#Cc4ccc(-c5ccc(-c6ccc(Br)s6)s5)s4)s3)s2)s1]

(6)

115 mg (0.25 mmol) of 2-iodo-5"-bromo(5,2':5',2"-terthiophene) (5) obtained above in the preceding step, and also 10 mg of bis(triphenylphosphine)-palladium(II) chloride (Pd (Cl$_2$)(PPh$_3$)$_2$) (30 μmol) and 8 mg of CuI (40 μmol) were introduced into a round-bottomed flask. The round-bottomed flask was then purged 3 times (vacuum/argon). 50 ml of distilled benzene, 0.36 ml of DBU (7 equivalents, 1.75 mmol), 15 μl of TMSA (0.5 equivalent, 0.13 mmol) and 3 μl of distilled water (0.4 eq.) were added in this order to the reaction medium. The mixture was left stirring for 24 h in the dark at ambient temperature. The solvent was then evaporated under reduced pressure, then the crude product was purified by passing through a chromatographic column (eluent: dichloromethane 5 L). The product was isolated in the form of a dark brown powder (44 mg, yield: 49%). This compound was directly inserted into the following reaction.

3) Third Step: Synthesis of [1,1',1",1'''-(η4-cyclobutadiene-tetrakis 1,2,3,4-[2,5,2',5',2"-terthiophene-5"-bromo])](η5-cyclopentadienyl)cobalt(I)

In a sealed tube, 44 mg (2 eq., 0.06 μmol) of bis(2,2':5',2"-terthiophene-5"-bromo)acetylene (6) obtained above in the second step and 15 mg of the compound (3) obtained above in step 3) of example 1 (1.5 equivalents, 0.04 μmol) were diluted in 1 ml of ethanol and 14 ml of THF. The reaction medium was heated at 150° C. using a microwave (90 watts, stationary regime) for 45 min. The solvents were then evaporated under reduced pressure, and then the crude product was filtered with ethanol (25 ml). The resulting cake was filtered with dichloromethane, to give the expected product in the form of a black powder (30 mg, yield: 32%).

$^1$H NMR (400 MHz, CDCl$_3$) δ 7.26 (d, J=3.6; 8H); 7.16 (dd, J=3.5; 8.4; 8H); 7.23-6.99 (m, 8H); 4.85 (s, 5H).
$^{13}$C NMR (101 MHz, CDCl$_3$) δ 132.77; 131.86; 131.12; 130.58; 130.07; 126.36; 126.08; 125.08; 124.38; 123.91; 123.67; 123.19; 85.31; 68.40.

Example 4

Synthesis of [1,1',1",1'''-(η4-1,3-cyclobutadiene-1,2,3,4-tetrayl)tetrakis-[benzene]](η5-cyclopentadienyl) cobalt(I)

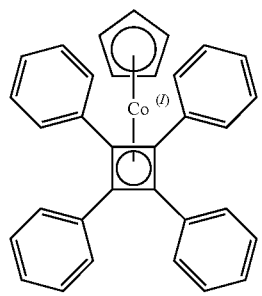

In a sealed tube, 45 mg of diphenylacetylene (2 equivalents, 250 mol) and 49 mg of the compound (3) as prepared above in step 3) of example 1 were diluted in 1 ml of ethanol and 14 ml of THF. The reaction medium was heated at 150° C. using a microwave (90 watts, stationary regime) for 45 min. The solvents were then evaporated under reduced pressure, and then the crude product was filtered with ethanol (25 ml). The resulting cake was filtered with dichloromethane. The filtrate of this second filtration was concentrated under reduced pressure to give a yellow powder of the expected product (60 mg, yield: 99%).

$^1$H NMR (400 MHz, CDCl$_3$) δ 4.65 (s, 5H); 7.20-7.26 (m, 12H); 7.46-7.48 (m, 8H).
$^{13}$C NMR (101 MHz, CDCl$_3$) δ 75.0 (4C); 83.3 (5C); 126.3 (4C); 128.0 (8C); 129.0 (8C); 136.6 (4C). These spectra are in agreement with the preceding ones in the literature: A. Geny et al., Ang. Chem. Int. Ed., 2009, 48(10), 1810-1813.

Example 5

Synthesis of [1,1',1",1'''-(η4-1,3-cyclobutadiene-1,2,3,4-tetrayl)tetrakis[4-n-butylbenzene]](η5-cyclopentadienyl)cobalt(I)

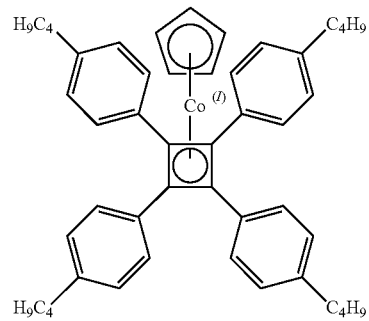

The general protocol of [2+2] complexation/cyclization used above in example 4 was applied here to 250 mg (0.98 mmol) of bis[4-n-butylbenzene]-acetylene and 185 mg (0.62 mmol) of compound (3) as prepared above in step 3) of example 1, in order to give the expected product in the form of a yellow powder (330 mg, yield=95%).

$^1$H NMR (400 MHz, CDCl$_3$) δ 7.37 (d, J=8.0 Hz, 8H); 7.02 (d, J=8.0 Hz, 8H); 4.61 (s, 5H); 2.58 (dd, J=8.0 Hz, 8H); 1.65 (dt, J=15.4; 7.6 Hz, 8H); 1.46-1.36 (m, 12H); 0.97 (t, J=7.3 Hz, 2H).
$^{13}$C NMR (101 MHz, CDCl$_3$) δ 140.63; 133.86; 128.72; 127.83; 83.00; 74.79; 35.60; 33.35; 22.58; 14.03.

Example 6

Synthesis of [1,1',1",1'''-(η4-1,3-cyclobutadiene-1,2,3,4-tetrayl)tetrakis[3,5-dimethoxybenzene]](η5-cyclopentadienyl)cobalt(I)

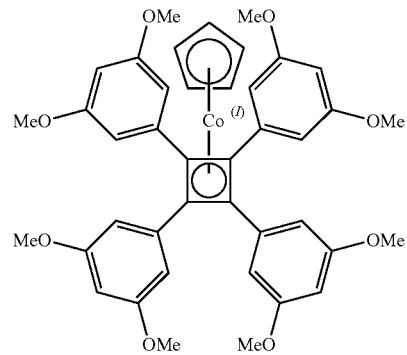

1) First Step: Synthesis of 1-(2,2-dibromovinyl)-3,5-dimethoxybenzene (7)

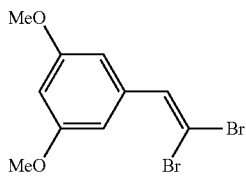

(7)

2.9 g (9 mmol) of tetrabromomethane were dissolved with 20 ml of distilled dichloromethane in a first round-bottomed flask purged three times with vacuum/argon. 4.39 g of triphenylphosphine were dissolved with 20 ml of distilled dichloromethane in a second round-bottomed flask purged three times with vacuum/argon. The solution of tetrabromomethane was then added dropwise at 0° C. to the triphenylphosphine solution. The resulting mixture, colored bright orange, was left stirring for 15 min.

1.5 g (9 mmol) of 3,5-dimethoxybenzaldehyde were dissolved with 20 ml of distilled dichloromethane in a round-bottomed flask purged three times with vacuum/argon. This solution was then added to the preceding one, and then the mixture was thus left stirring for 2 hours at ambient temperature. The reaction medium was then stirred with water and then extracted three times with 50 ml of dichloromethane. The organic phase was then dried over sodium sulfate and then the crude solvent was evaporated under reduced pressure. The crude product of the reaction was then purified by column chromatography using, as eluent, a petroleum ether/dichloromethane (7/3: v/v) mixture. The product was then isolated in the form of a transparent solid (m=2.02 g; yield=70%).

$^1$H NMR (400 MHz, CD$_3$CN) δ 7.42 (s, 1H); 6.69 (dd, J=2.3; 0.5 Hz, 2H); 6.45 (t, J=2.3 Hz, 1H); 3.80 (s, 6H). This spectrum is in agreement with the preceding ones published by W. H. Moser et al., J. Org. Chem., 2006, 71(17), 6542-6546.

1) Second Step: Synthesis of 1-ethynyl-3,5-dimethoxybenzene (8)

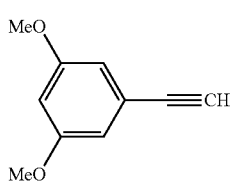

(8)

2.02 g (6.3 mmol) of compound (7) obtained above in the preceding step were deposited in a round-bottomed flask then purged three times with vacuum/argon. The solid was then dissolved in THF and cooled to −78° C. Next, 19.6 ml of a 1.4 M solution of butyllithium in hexane were added. The mixture was left stirring at −78° C. for 1 hour, then at −40° C. for 2 hours. The mixture was then brought back to ambient temperature, the excess of butyllithium was neutralized with 5 ml of methanol, then the reaction medium was stirred with water and extracted three times with 50 ml of dichloromethane. The organic phase was then dried over sodium sulfate and then the solvent was evaporated under reduced pressure. The expected product was obtained in the form of a yellow powder (m=1.07 g, yield=99%).

$^1$H NMR (400 MHz, CDCl$_3$) δ 6.65 (s, 2H); 6.47 (s, 1H); 3.78 (s, 6H); 3.04 (s, 1H). This spectrum is in agreement with the one given by J. Kalisiak, et al., Org. Lett., 2008, 10(15), 3171-3174.

3) Third Step: Synthesis of bis(3,5-dimethoxybenzene)acetylene (9)

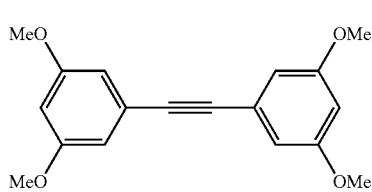

(9)

810 mg (5 mmol) of the compound (8) obtained above in the preceding step, 1.09 mg (5 mmol) of 3,5-dimethoxyiodobenzene, 10 mg (50 μmol) of cupric iodide and 35 mg (50 μmol) of bis(triphenylphosphine)palladium(II) chloride were added to a round-bottomed flask. The round-bottomed flask was then purged 3 times with argon. 40 ml of distilled triethylamine were then added and the mixture was then stirred for 24 hours. The reaction medium was then diluted with 60 ml of a 6M solution of hydrochloric acid then extracted three times with 50 ml of dichloromethane. The organic phase was washed with 100 ml of a 1M solution of sodium hydroxide, then dried over sodium sulfate and the solvent was evaporated under reduced pressure. The crude product of the reaction was then purified by column chromatography using, as eluent, a petroleum ether/dichloromethane (1/1: v/v) mixture. The expected product was then isolated in the form of a yellow powder (m=0.99 g; yield=66%).

$^1$H NMR (400 MHz, CDCl$_3$) δ 6.70 (d, J=2.3 Hz, 4H); 6.47 (t, J=2.3 Hz, 2H); 3.81 (s, 12H). This spectrum was in agreement with those previously obtained by Y. T. Wu et al., Angew. Chem. Int. Ed., 2008, 47(51), 9891-9894.

4) Fourth Step: Synthesis of [1,1',1'',1'''-(η4-1,3-cyclobutadiene-1,2,3,4-tetrayl)tetrakis[3,5-dimethoxybenzene]](η5-cyclopentadienyl)cobalt(I)

The general protocol of [2+2] complexation/cyclization used above in example 4 was applied here to 75 mg (0.25 mmol) of compound (9) obtained above in the preceding step and 56.3 mg (1.5 equivalents, 0.19 mmol) of compound (3) as prepared above in step 3) of example 1, in order to give the expected product in the form of a yellow powder (90 mg, yield=99%).

$^1$H NMR (400 MHz, CDCl$_3$) δ 6.71 (d, J=2.2 Hz, 8H); 6.35 (t, J=2.2 Hz, 4H); 4.67 (s, 5H); 3.68 (s, 12H).

$^{13}$C NMR (101 MHz, CDCl$_3$) δ 160.14; 138.19; 107.09; 99.20; 83.28; 75.06; 55.25.

Example 7

Synthesis of [1,1'-[(1,2,3,4-η)-2,4-bis(4-methoxybenzene)-1,3-cyclobutadien-1,3-diyl]bis[phenyl]](η5-2,4-cyclopentadien-1-yl)cobalt(I)

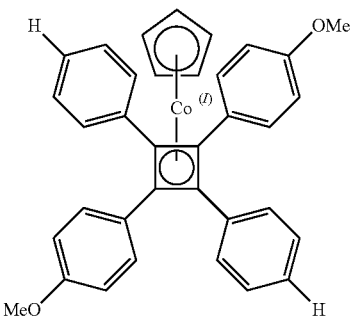

1) First Step: Synthesis of 1-methoxy-4-phenylethynylbenzene (10)

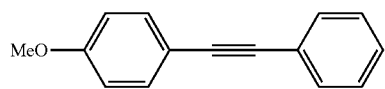

(10)

112 mg (1.1 mmol) of ethynylbenzene, 259 mg (1.1 mmol) of 4-methoxy-iodobenzene, 2 mg (10 μmol) of cupric iodide and 8 mg (10 μmol) of bis(triphenylphosphine)palladium(II) chloride were added to a round-bottomed flask. The round-bottomed flask was then purged 3 times with argon. 20 ml of distilled triethylamine were then added and the mixture was then stirred for 24 hours. The reaction medium was then diluted with 20 ml of a 6M solution of hydrochloric acid then extracted three times with 20 ml of dichloromethane. The organic phase was washed with 40 ml of a 1M solution of sodium hydroxide, then dried over sodium sulfate and the solvent was evaporated under reduced pressure. The crude product of the reaction was then purified by column chromatography using, as eluent, a petroleum ether/dichloromethane (7/3; v/v) mixture. The expected product was then isolated in the form of a yellow powder (m=201 mg; yield=97%).

$^1$H NMR (400 MHz, CDCl$_3$) δ 7.51 (d, J=7.8 Hz, 2H); 7.47 (d, J=8.9 Hz, 2H); 7.33 (m, 3H); 6.88 (d, J=8.9 Hz, 2H); 3.83 (s, 3H). This spectrum was in agreement with that obtained by B. H. Lipshutz et al., Organic Letters, 2008, 10(17), 3793-3796.

2) Second Step: Synthesis of [1,1'-[(1,2,3,4-η)-2,4-bis(4-methoxybenzene)-1,3-cyclobutadien-1,3-diyl]bis[phenyl]](η5-2,4-cyclopentadien-1-yl)cobalt(I)

The general protocol of [2+2] complexation/cyclization used above in example 4 was applied here to 21 mg (0.1 mmol) of compound (10) obtained above in the preceding step and 23 mg (1.5 equivalents, 75 μmol) of compound (3) as prepared above in step 3) of example 1, in order to give the expected product in the form of a yellow powder (27 mg, yield=99%).

$^1$H NMR (400 MHz, C$_6$D$_6$) δ 7.78 (d, J=6.2 Hz, 4H); 7.67 (d, J=8.2 Hz, 4H), 7.19 (m, 6H), 6.79 (d, J=8.7 Hz, 4H), 4.68 (s, 5H), 3.41 (s, 6H).

$^{13}$C NMR (101 MHz, CDCl$_3$) δ 157.99; 136.91; 130.13; 129.98; 128.75; 128.60; 127.88; 125.95; 113.48; 82.98; 55.20; 29.70.

Example 8

Synthesis of [1,1'-[(1,2,3,4-η)-2,4-bis(4-nitrobenzene)-1,3-cyclobutadien-1,3-diyl]bis[phenyl]](η5-2,4-cyclopentadien-1-yl)cobalt(I)

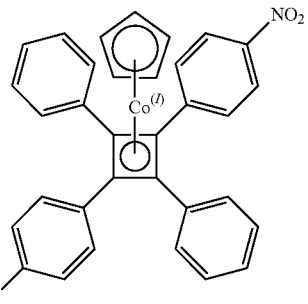

1) First Step: Synthesis of 1-nitro-4-phenylethynylbenzene

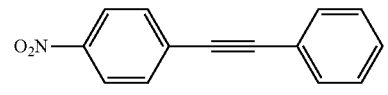

(11)

112 mg (1.1 mmol) of ethynylbenzene, 274 mg (1.1 mmol) of 4-nitro-iodobenzene, 2 mg (10 μmol) of cupric iodide and 8 mg (10 μmol) of bis(triphenylphosphine)palladium(II) chloride were added to a round-bottomed flask. The round-bottomed flask was then purged 3 times with argon. 20 ml of distilled triethylamine were then added and the mixture was then stirred for 24 hours. The reaction medium was then diluted with 20 ml of a 6M solution of hydrochloric acid then extracted three times with 20 ml of dichloromethane. The organic phase was washed with 40 ml of a 1M solution of sodium hydroxide, then dried over sodium sulfate and the solvent was evaporated under reduced pressure. The crude product of the reaction was then purified by column chromatography using, as eluent, a petroleum ether/dichloromethane (8/2; v/v) mixture. The expected product (11) was then isolated in the form of a yellow powder (m=217 mg; yield=88%).

$^1$H NMR (400 MHz, CDCl$_3$) δ 8.25 (d, J=9.0 Hz, 2H); 7.70 (d, J=9.0 Hz, 2H); 7.62-7.56 (m, 2H), 7.45-7.40 (m, 3H). This spectrum was in agreement with that previously obtained by T. Mino et al., J. Org. Chem., 2006, 71(25), 9499-9502.

2) Second Step: Synthesis of [1,1'-[(1,2,3,4-η)-2,4-bis(4-nitrobenzene)-1,3-cyclobutadien-1,3-diyl]bis[phenyl]](η5-2,4-cyclopentadien-1-yl)cobalt(I)

The general protocol of [2+2] complexation/cyclization was applied here to 23 mg (0.1 mmol) of compound (11)

obtained above in the preceding step and 23 mg of compound (3) (1.5 equivalents, 75 µmol) obtained at the end of step 3) of example 1. The crude product was then purified by chromatography using, as eluent, a petroleum ether/dichloromethane (1/1: v/v) mixture. The expected product was then isolated in the form of a red powder (m=27 mg; yield=94%).

$^1$H NMR (400 MHz, CDCl$_3$) δ 8.05 (d, J=9.0 Hz, 4H); 7.53 (d, J=8.1 Hz, 4H); 7.48 (d, J=9.0 Hz, 4H); 7.45-7.36 (m, 6H); 4.72 (s, 5H).

$^{13}$C NMR (101 MHz, CDCl$_3$) δ 145.56; 145.21; 134.10; 129.62; 128.90; 128.40; 127.97; 127.58; 83.63; 71.86; 29.72.

Figure 2:
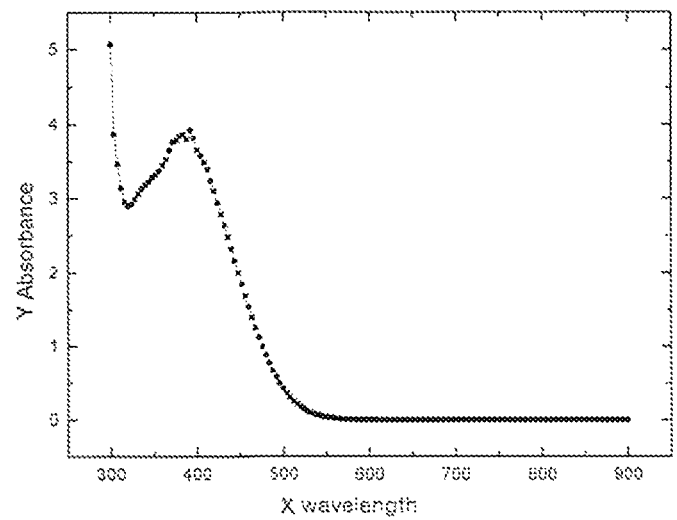
FIG. 2 is an absorbance graph from Example 8, in accordance with one embodiment.

The absorption spectrum of this compound was measured with a UV-visible spectrophotometer sold by the company Perkin Elmer under the reference Lambda 650, in solution at 0.1 mmol/ml in dichloromethane. It is reported in appended FIG. 2, in which the absorbance in arbitrary units is a function of the wavelength in nm ($\lambda_{max}$=388 nm; ε=4.1×10$^4$ cm$^{-1}$·L·mol$^{-1}$; Egap=2.3 eV).

Example 9

Synthesis of [1,1'-[(1,2,3,4-η)-2,4-bis(4-nitrobenzene)-1,3-cyclobutadien-1,3-diyl]bis[4-methoxbenzene]](η5-2,4-cyclopentadien-1-yl)cobalt(I)

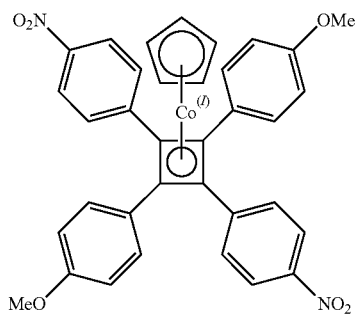

1) First Step: Synthesis of 1-nitro-4-(4-methoxyethynylbenzene)benzene

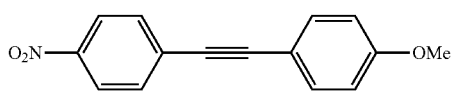

(12)

500 mg (3.8 mmol) of compound (10) as prepared above in step 1) of example 7, 940 mg (3.8 mmol) of 4-nitroiodobenzene, 8 mg (38 µmol) of cupric iodide and 30 mg (38 µmol) of bis(triphenylphosphine)palladium(II) chloride were added to a round-bottomed flask. The round-bottomed flask was then purged 3 times with argon. 40 ml of distilled triethylamine were added and the mixture was then stirred for 24 hours. The reaction medium was then diluted with 60 ml of a 6M solution of hydrochloric acid then extracted three times with 50 ml of dichloromethane. The organic phase was washed with 100 ml of a 1M solution of sodium hydroxide, then dried over sodium sulfate and the solvent was evaporated under reduced pressure. The expected product was obtained in the form of a yellow powder (m=98 mg; yield=99%).

$^1$H NMR (400 MHz, CDCl$_3$) δ 8.18 (d, J=9.0 Hz, 2H); 7.61 (d, J=9.0 Hz, 2H); 7.49 (d, J=8.9 Hz, 2H); 6.90 (d, J=8.9 Hz, 2H); 3.83 (s, 3H).

$^{13}$C NMR (101 MHz, CDCl$_3$) δ 160.44; 146.67; 133.44; 131.97; 130.68; 123.60; 114.22; 114.12; 95.17; 86.66; 55.36. This spectrum is in agreement with that previously obtained by Y. Nishihara et al., Tet. Lett., 2009, 50(32), 4643-4646.

2) Second Step: Synthesis of [1,1'-[(1,2,3,4-η)-2,4-bis(4-nitrobenzene)-1,3-cyclo-butadien-1,3-diyl]bis[4-methoxybenzene]](η5-2,4-cyclopentadien-1-yl)cobalt(I)

The general protocol of [2+2] complexation/cyclization was applied here to 63 mg (0.25 mmol) of compound (12) obtained above in the preceding step and 56 mg of compound (3) as obtained above in step 3) of example 1 (1.5 equivalents, 190 µmol). The crude product was then purified by chromatography using, as eluent, a petroleum ether/dichloromethane (1/1: v/v) mixture. The expected product was then isolated in the form of a red powder (m=74 mg; yield=95%).

$^1$H NMR (400 MHz, CDCl$_3$) δ 8.03 (d, J=8.5 Hz, 4H); 7.47 (dd, J=8.4, 6.4 Hz, 8H); 6.92 (d, J=8.5 Hz, 4H); 4.68 (s, 5H); 3.90 (s, 6H).

$^{13}$C NMR (101 MHz, CDCl$_3$) δ 159.01; 145.77; 145.42; 130.95; 127.65; 125.74; 123.49; 114.07; 83.39; 77.21; 72.11; 55.35.

Figure 3:
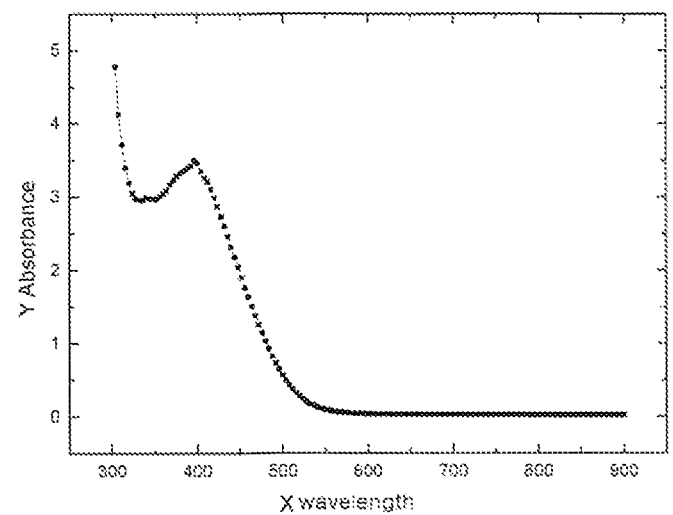
FIG. 3 is an absorbance graph from Example 9, in accordance with one embodiment.

The absorption spectrum of this compound was measured with a UV-visible spectrophotometer sold by the company Perkin Elmer under the reference Lambda 650, in solution at 0.1 mmol/ml in dichloromethane. It is reported in appended FIG. 3, in which the absorbance in arbitrary units is a function of the wavelength in nm ($\lambda_{max}$=396 nm; ε=3.4×10$^4$ cm$^{-1}$·L·mol$^{-1}$; Egap=2.1 eV).

Example 10

Synthesis of [1,1'-[(1,2,3,4-η)-2,4-bis(4-bromobenzene)-1,3-cyclobutadien-1,3-diyl]bis[4-methoxybenzene]](η5-2,4-cyclopentadien-1-yl)cobalt(I)

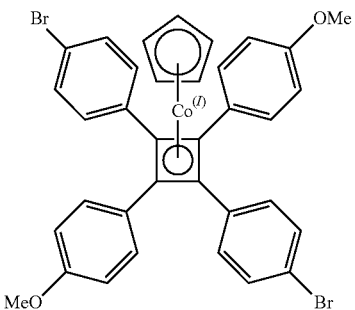

1) First Step: Synthesis of 1-methoxy-4-(4-bromoethynylbenzene)benzene

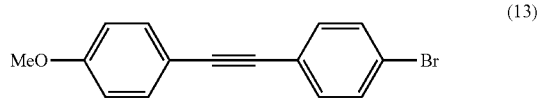 [SMILES: COc1ccc(C#Cc2ccc(Br)cc2)cc1]

(13)

200 mg (1.1 mmol) of compound (10) as prepared above in step 1) of example 7, 259 mg (1.1 mmol) of 4-methoxyiodobenzene, 2 mg (10 μmol) of cupric iodide and 8 mg (10 μmol) of bis(triphenylphosphine)palladium(II) chloride were added to a round-bottomed flask. The round-bottomed flask was then purged 3 times with argon. 20 ml of distilled triethylamine were added and the mixture was then stirred for 24 hours. The reaction medium was then diluted with 20 ml of a 6M solution of hydrochloric acid then extracted three times with 20 ml of dichloromethane. The organic phase was washed with 40 ml of a 1M solution of sodium hydroxide, then dried over sodium sulfate and the solvent was evaporated under reduced pressure. The crude product of the reaction was then purified by column chromatography using, as eluent, a petroleum ether/dichloromethane (1/1; v/v) mixture. The expected product was then isolated in the form of a yellow powder (m=287 mg; yield=99%).

$^1$H NMR (400 MHz, CD$_3$CN) δ 7.50-7.42 (d+d J=8.9, 8.4 Hz, 4H); 7.36 (d, J=8.4 Hz, 2H); 6.88 (d, J=Hz, 2H); 3.83 (s, 3H). This spectrum is in agreement with that previously obtained by G. W. Kabalka, et al., Tet. Lett., 2006, 47(7), 1133-1136.

Example 11

Synthesis of [1,1',1'',1'''-(η4-1,3-cyclobutadiene-1,2,3,4-tetrayl)tetrakis[4-methyl benzoate]](η5-cyclopentadienyl)cobalt(I)

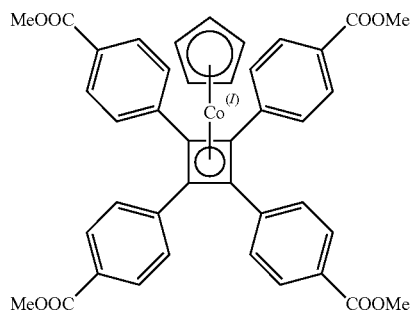

1) First Step: Synthesis of dimethyl 4,4'-(ethyne-1,2-diyl)dibenzoate

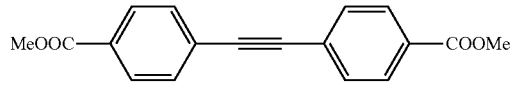

(14)

1 g (3.8 mmol) of 4-iodobenzoic acid methyl ester, 72 mg (0.39 mmol) of cupric iodide and 154 mg (0.22 mmol) of bis(triphenylphosphine)palladium(II) chloride were added to a round-bottomed flask. The round-bottomed flask was then purged 3 times with argon. 80 ml of distilled benzene, 4 g (26.6 mmol) of 1,8-diazabicyclo[5.4.0]undec-7-ene, 0.2 g (1.9 mmol) of trimethylsilylacetylene and 22 μl (1.5 mmol) of water were added and the mixture was then stirred for 24 hours in the dark. The reaction medium was then diluted with 20 ml of a 6M solution of hydrochloric acid then extracted three times with 20 ml of dichloromethane. The organic phase was washed with 40 ml of a 1M solution of sodium hydroxide, then dried over sodium sulfate and the solvent was evaporated under reduced pressure. The crude product of the reaction was then purified by column chromatography using, as eluent, a petroleum ether/ethyl acetate (3/1; v/v) mixture. The expected product was then isolated in the form of a white powder (m=394 mg; yield=72%).

$^1$H NMR (400 MHz, CDCl$_3$) δ 7.97 (d, J=8.5 Hz, 1H); 7.53 (d, J=8.5 Hz, 1H); 3.86 (s, 2H).

This spectrum was in agreement with that previously obtained by Y. T. Wu et al., Angew. Chem. Int., Ed. 2008, 47(51), 9891-9894.

2) Second Step: Synthesis of [1,1',1'',1'''-(η4-1,3-cyclobutadiene-1,2,3,4-tetrayl)tetrakis[4-methyl benzoate]](η5-cyclopentadienyl)cobalt(I)

The general protocol of [2+2] complexation/cyclization was applied here to 100 mg (0.34 mmol) of compound (14) obtained above in the preceding step and 76 mg of compound (3) obtained above in step 3) of example 1 (1.5 equivalents, 0.25 mmol), in order to give the expected product in the form of a yellow powder (96 mg; 80% yield).

$^1$H NMR (400 MHz, CDCl$_3$) δ 7.90 (d, J=8.5 Hz, 8H); 7.46 (d, J=8.5 Hz, 8H); 4.65 (s, 5H); 3.93 (s, 12H).

$^{13}$C NMR (101 MHz, CDCl$_3$) δ 167.00; 141.20; 129.63; 128.68; 128.47; 83.86; 77.48; 77.16; 76.84; 74.91; 52.31.

Example 12

Synthesis of [1,1',1'',1'''-(η4-1,3-cyclobutadiene-1,2,3,4-tetrayl)tetrakis[2,2',5'-bithiophene]](η5-cyclopentadienyl)cobalt(I)

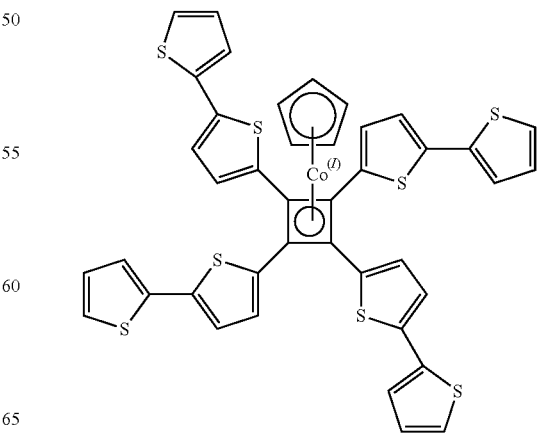

1) First Step: Synthesis of 5-(2,2-dibromoethenyl)-2,2'-bithiophene

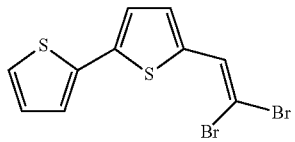

(15)

3.4 g (10.2 mmol) of tetrabromomethane were dissolved with 20 ml of distilled dichloromethane in a first round-bottomed flask purged with argon. 5.4 g (20.4 mmol) of triphenylphosphine were dissolved with 20 ml of distilled dichloromethane in a second round-bottomed flask purged three times with argon. The tetrabromomethane solution was added dropwise at 0° C. to the triphenylphosphine solution. The resulting mixture, colored bright orange, was left stirring for 15 min.

At the same time, 1 g (5.1 mmol) of 2-(carboxaldehyde)(5,2'-bithiophene) was dissolved with 20 ml of distilled dichloromethane in a round-bottomed flask purged three times with argon. This solution was then added to the mixture of the tetrabromomethane solution and of the triphenylphosphine solution, and then the resulting mixture was thus left stirring for 2 hours at ambient temperature. The reaction medium was then stirred with water and then extracted three times with 50 ml of dichloromethane. The organic phase was then dried over sodium sulfate and then the solvent was evaporated under reduced pressure. The crude product of the reaction was then purified by column chromatography using dichloromethane as eluent. The expected product (15) was then isolated in the form of a yellow solid (m=1.55 g; yield=90%).

$^1$H NMR: (CDCl$_3$, 400 MHz): δ 7.03 (dd, 1H); 7.09 (d, H); 7.13 (d, 1H); 7.24 (d, 1H); 7.27 (d, 1H).

This spectrum is in agreement with that previously obtained by T. B. Patrick et al., J. Org. Chem., 1974, 39(25), 3791-2.

2) Second Step: Synthesis of 5-ethynyl-2,2'-bithiophene

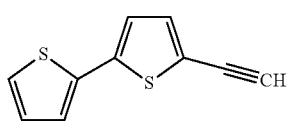

(16)

1.55 g (4.6 mmol) of compound (15) obtained above in the preceding step were deposited in a round-bottomed flask then purged three times with argon. The solid was then dissolved in THF and cooled to −78° C. Next, 3.68 ml of a 2.5 M solution of butyllithium in hexane were added. The mixture was left stirring at −78° C. for 1 hour, then at −40° C. for 2 hours. The mixture was then brought back to ambient temperature, the excess of butyllithium was neutralized with 5 ml of methanol, then the reaction medium was stirred with water and extracted three times with 50 ml of dichloromethane. The organic phase was then dried over sodium sulfate and then the solvent was evaporated under reduced pressure. The crude product of the reaction was then purified by column chromatography using petroleum ether as eluent. The expected product (16) was obtained in the form of a black solid (m=624 mg, yield=71%).

$^1$H NMR: (CDCl$_3$, 400 MHz): δ 7.25 (dd J=1.2; 5.1 Hz, 1H); 7.19 (dd, J=1.2; 3.6 Hz, 1H); 7.18 (dd, J=0.5; 3.6 Hz, 1H); 7.01-7.04 (m, 2H); 3.40 (d, J=0.5 Hz). This spectrum is in agreement with that previously obtained by T. B. Patrick, et al., J. Org. Chem., 1974, 39(25), 3791-2.

3) Third Step: Synthesis of bis-2-(5,2'-bithiophene)acetylene

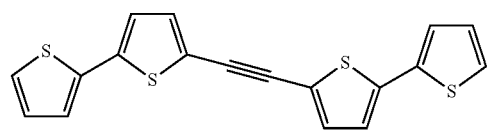

(17)

0.291 mg (1.5 mmol) of the compound (16) obtained above in the preceding step, 444 mg (1.5 mmol) of 2-iodo(5,2'-bithiophene), 3 mg (15 µmol) of cupric iodide and 11 mg (15 µmol) of bis(triphenylphosphine)palladium(II) chloride were added to a round-bottomed flask. The round-bottomed flask was then purged 3 times with argon. 40 ml of distilled triethylamine were added and the mixture was then stirred for 24 hours. The reaction medium was then diluted with 60 ml of a 6M solution of hydrochloric acid then extracted three times with 50 ml of dichloromethane. The organic phase was washed with 100 ml of a 1M solution of sodium hydroxide, then dried over sodium sulfate and the solvent was evaporated under reduced pressure. The crude product of the reaction was then purified by column chromatography (eluent: petroleum ether). The expected product (17) was then isolated in the form of a yellow powder (m=512 g; yield=96%).

$^1$H NMR (400 MHz, CDCl$_3$) δ 7.25 (d, J=5.1 Hz, 2H); 7.20 (d, J=3.6 Hz, 2H); 7.18 (d, J=3.8 Hz, 2H); 7.07 (d, J=3.8 Hz, 2H); 7.20 (dd, J=5.1; 3.6 Hz, 2H). This spectrum is in agreement with that previously obtained by J. Nakayama et al., Heterocycles, 1992, 34(8), 1487-90.

4) Fourth Step: Synthesis of [1,1',1",1'''-(η4-1,3-cyclobutadiene-1,2,3,4-tetrayl)tetrakis[2,2',5'-bithiophene]](η5-cyclopentadienyl)cobalt(I)

The general protocol of [2+2] complexation/cyclization was applied here to 51 mg (0.145 mmol) of compound (17) obtained above in the preceding step and 28 mg of compound (3) obtained above in step 3) of example 1 (1.5 equivalents, 0.11 mmol), in order to give the expected product in the form of a black powder (53 mg; 83% yield).

$^1$H NMR (400 MHz, CDCl3) δ 7.26 (m, 4H), 7.10 (d, J=3.7, 4H); 7.05-7.00 (m, 8H); 4.85 (s, 5H).

Figure 4:
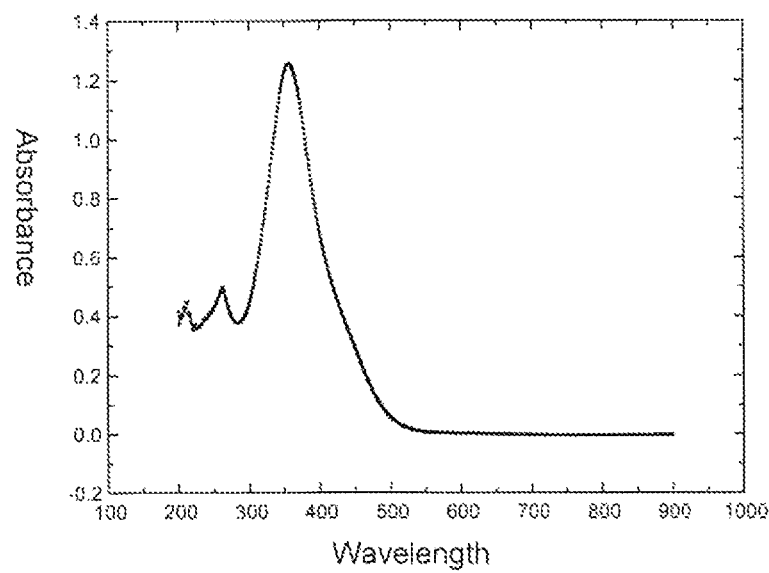
FIG. 4 is an absorbance graph from Example 12, in accordance with one embodiment.

The absorption spectrum of this compound was measured with a UV-visible spectrophotometer sold by the company Perkin Elmer under the reference Lambda 650, in solution at 0.24 mmol/ml in dichloromethane. It is reported in appended FIG. 4, in which the absorbance in arbitrary units is a function of the wavelength in nm ($\lambda_{max}$=354 nm; ε=5.1×10$^4$ cm$^{-1}$·L·mol$^{-1}$; Egap=2.0 eV).

Example 13

Preparation of Photovoltaic Conversion Cells and Studies of their Properties Various photovoltaic conversion cells using various compounds of formula (I) were prepared. The general protocol for preparing these cells was the following.

A glass sheet (25×23 mm) covered with a layer of ITO as positive electrode (10-100 Ω/sq, Sigma Aldrich) was partially etched with a solution of hydrochloric acid at 18% by vol and of Fe(Cl$_3$), at ambient temperature for one minute. The thus etched sheet was washed with a cleaning agent based on anionic and nonionic surfactants, stabilizers, alkalis and sequestrants, sold under the trade name Decon 90® by the company DECON, then with acetone (20 min, ultrasound), ethanol (20 min, ultrasound), and under UV/O$_3$ irradiation for 30 min.

A 20 nm layer of PEDOT:PSS was then deposited via a wet method (spin coating, 22 μl of a solution containing 4.05 ml of PEDOT:PSS in 4.95 ml of water, then, where necessary, annealed at 110° C. for 30 min (see table I) in a tube furnace under a stream of nitrogen). An 80 nm active layer was then deposited via a wet method from a solution comprising a compound of formula (I) and PCBM in 1,2-dichloromethane for cells no. 4, 5 and 6 or in chlorobenzene for cells no. 1, 2 and 3 (spin coating, 150 s, 200 rpm, solutions at various compound of formula (I)/PCBM weight ratios). An annealing of 30 min at 120° C. was then optionally carried out in a tube furnace under a stream of nitrogen (see table I). Next, a 0.8 nm layer of LiF (buffer layer) and an 80 nm layer of aluminum (negative electrode) were deposited by evaporation, in an ultra-high vacuum chamber.

In this example the compounds of formula (I) used are [1,1',1'',1'''-(η4-cyclobutadiene-1,2,3,4-tetrayl)tetrakis[2,2',5',2'',5''-terthiophene]](η5-cyclopenta-dienyl)cobalt(I) as prepared above in example 1 and [1,1'-[(1,2,3,4-η)-2,4-bis(4-nitrobenzene)-1,3-cyclobutadien-1,3-diyl]bis[4-methoxy-benzene]](η5-2,4-cyclo-pentadien-1-yl)cobalt(I) as prepared above in example 9.

The various cells prepared are given in detail in table 1 below:

TABLE 1

| Cell | Compound of formula (I) | Compound (I)/PCBM weight ratio | Concentration of the solution of active layer (mg/ml) | Active layer deposition rate | Annealing of PEDOT:PSS | Annealing of the active layer |
|---|---|---|---|---|---|---|
| 1 | Ex. 9 | 1/1 | 30 | 1000 rpm/50 s | yes | no |
| 2 | Ex. 1 | 1/1 | 30 | 500 rpm/30 s | yes | no |
| 3 | Ex. 1 | 1/1 | 30 | 500 rpm/50 s | yes | yes |
| 4 | Ex. 1 | 1/2 | 25 | 200 rpm/150 s | yes | no |
| 5 | Ex. 1 | 1/4 | 40 | 200 rpm/150 s | yes | no |
| 6 | Ex. 1 | 1/2 | 15 | 200 rpm/150 s | no | no |

These various cells were then tested in photovoltaic conversion on a microtip station, under AM 1.5 lighting from a solar radiation simulator equipped with a 150 W xenon lamp sold by the company Lot Oriel. The measurements were carried out with a microtip station coupled to a sourcemeter (Keithley 2602 SourceMeter).

The standard surface area of the electrodes was between 0.03 mm$^2$ and 0.15 mm$^2$ and the incident surface power density was 75 or 100 mW/cm$^2$.

For each cell, a current-voltage curve (I=f(V)) was made in the dark and under illumination (not represented).

The form factor (FF) was calculated according to the following formula:

$$FF = \frac{P\max}{P\max_{abs}}$$

$$= \frac{Ipm \times Vpm}{Isc \times Voc}$$

wherein:
Pmax=maximum power measured
Pmax$_{abs}$=absolute maximum power
I$_{pm}$=intensity at maximum power
Vpm=voltage at maximum power
I$_{sc}$=short-circuit intensity
V$_{oc}$=short-circuit voltage The efficiency (η) of each of the cells was calculated according to the following formula:

$$\eta = \frac{P\max}{Pi}$$

$$= \frac{Ipm \times Vpm}{Pis \times S}$$

$$= \frac{FF \times Isc \times Voc}{Pis \times S}$$

wherein:
Pi=incident power
Pis=incident surface power
S=surface area of the electrode The performances of each of the cells are given in table 2 below:

TABLE 2

| Cell | V$_{oc}$ (mV) | Photovoltaic conversion efficiency (%) | FF (%) |
|---|---|---|---|
| 1 | 403 | 0.005 | 26 |
| 2 | 659 | 0.15 | 25 |
| 3 | 670 | 0.17 | 30 |
| 4 | 523 | 0.17 | 26 |
| 5 | 483 | 0.16 | 28 |
| 6 | 608 | 0.35 | 30 |

The values given in table 2 above are taken from quadrant 4 of the I=f(V) curves (lower right quarter, x-axes>0 and y-axes<0).

These results show that the photovoltaic conversion cells have a V$_{oc}$ that may reach 600 mV, which is comparable with that which is obtained with the currently best-performing cells in the current literature (Konarka P3HT/PCBM cell: V$_{oc}$<650 mV; C. J. Brabec et al., Adv. Mater., 2009, 21, 1323-1338).

The V$_{oc}$ is a marker of the adjustment of the electronic levels between the electron donor (compound of formula (I)) and the electron acceptor (here PCBM). The presence of the cobalt core plays a large part in this good positioning of the electronic levels of the compounds of formula (I). These results are very surprising insofar as the best conversion efficiencies are obtained with cells prepared without annealing, which is contrary to the teaching from the literature.

Example 14

Preparation of Two Photovoltaic Conversion Cells in Accordance with the Invention In this example, two photovoltaic conversion cells having different sizes of electrodes were prepared and tested using, in the active layer, the compound synthesized above in example 1 as electron donor and PCBM as electron acceptor.

The general protocol for preparing the photovoltaic cells given above in example 13 was used, with the following specificities:

- all the steps of manufacturing and testing the cell were carried out in a glove box in an inert atmosphere ($N_2$).
- deposition of a 20 nm PEDOT:PSS layer (22 µl, deposition of a drop of the solution, then spin coating at 2000 rpm for 50 s, with no annealing);
- deposition of a 100 nm active layer from a solution of the compound synthesized in example 1 (10 mg) and of PCBM (20 mg) in dichloromethane, said solution having been subjected to ultrasound waves for 20 min and filtered through a 0.2 µm PTFE filter (17 µl of solution, deposition of a drop of solution onto the sample, then spin coating at 350 rpm for 200 s, then at 2000 rpm for 5 s, no annealing);
- deposition of LiF via a gaseous method: evaporation of 8 Å of LiF;
- deposition of aluminum via a gaseous method: evaporation of 80 nm of Al.

Cell no. 7 was prepared according to this protocol using 7.5 mm² electrodes and an incident power of 75 mW and cell no. 8 using 5 mm² electrodes and an incident power of 100 mW.

Figure 5:
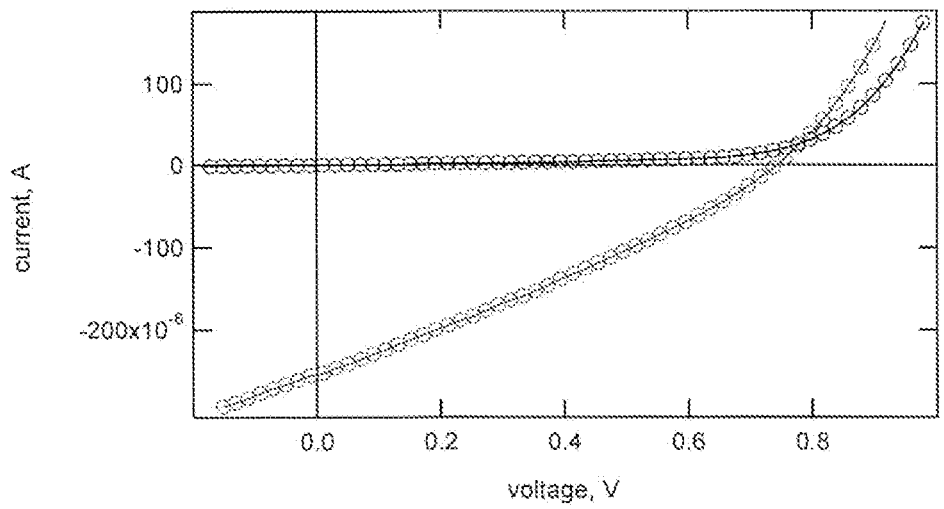
FIGS. 5-6 are plot curves of amps vs. Voltage from Example 14, in accordance with one embodiment.
Figure 6:
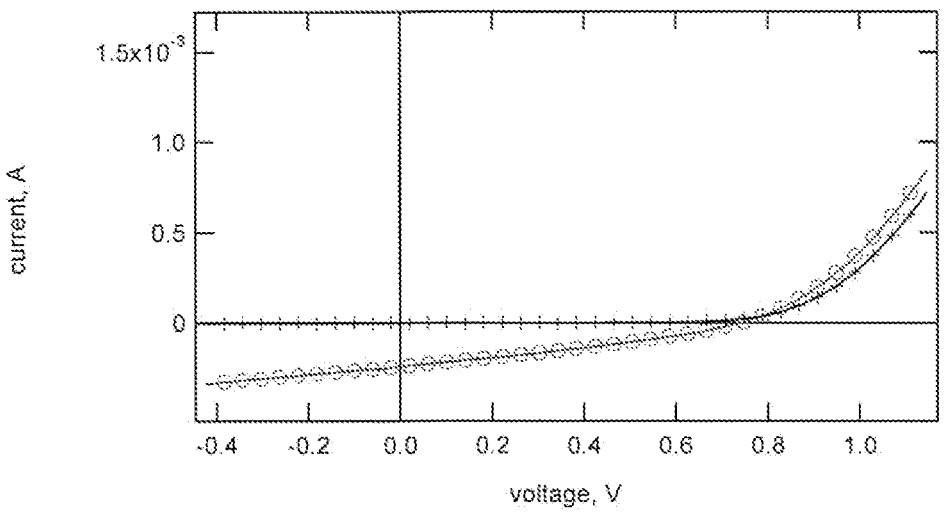

The curves obtained, I (in amperes)=f(V) (in volts), for each of the cells are given respectively by appended FIGS. 5 and 6.

In FIG. 5, the lowest curve corresponds to the current-voltage characteristic under illumination and the highest curve corresponds to the current-voltage characteristic in the dark. In FIG. 6, the curve plotted with the hollow circles (o) corresponds to the current-voltage characteristic under illumination and the curve plotted with the (+) signs corresponds to the current-voltage characteristic in the dark. The performances of each of the cells are reported in table 3 below:

TABLE 3

| Cell | $I_{sc}$ (mA) | $J_{sc}$ (mA/cm²) | $V_{oc}$ (mV) | FF (%) | η (%) |
|---|---|---|---|---|---|
| 7 | −0.254 | 3.38 | 739 | 29.2 | 0.98 |
| 8 | −0.241 | 4.87 | 737 | 31.3 | 1.11 |

These results demonstrate the very good performances of the photovoltaic cells in accordance with the invention. Indeed, the best photovoltaic conversion cells known at the present time in which the active layer is composed of a p-type compound (here compound of formula (I)) and of an n-type compound (here PCBM), which are both "small" molecules, i.e. non-polymeric compounds, generally result in a maximum efficiency of less than 1%.

The invention claimed is:

1. A method for the preparation of an active layer in a photovoltaic conversion cell, said method comprising the step of:

employing, as a electron donor and in combination with an electron acceptor, at least one cobalt complex of formula (I-a) or (I-b) below:

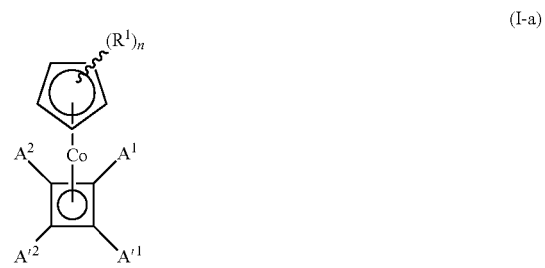

(I-a)

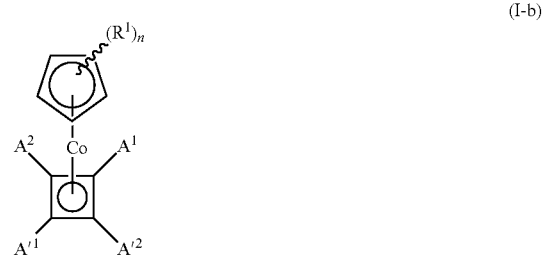

(I-b)

wherein:

n is an integer that varies from 0 to 5;

$R^1$ is chosen from I, $C_1$-$C_{12}$ alkyl, trimethylsilyl, HgCl, —C(O)($C_1$-$C_4$)alkyl, and an oxazole group optionally substituted by a $C_1$-$C_4$ alkyl radical, it being understood that when n>1, all the $R^1$ radicals of a given compound of formula (I-a) or (I-b) are identical, the groups $A^1$, $A'^1$, $A^2$ and $A'^2$ are identical in pairs and are chosen from the groups of formulae (II-1) to (II-9) below:

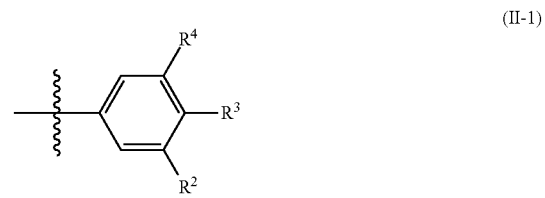

(II-1)

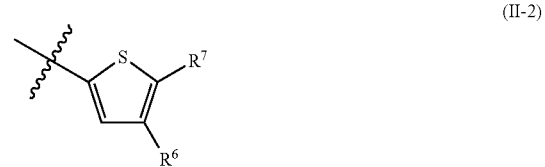

(II-2)

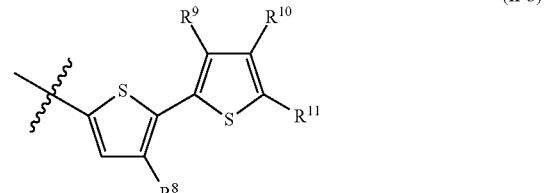

(II-3)

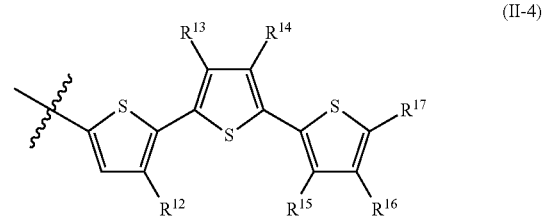

(II-4)

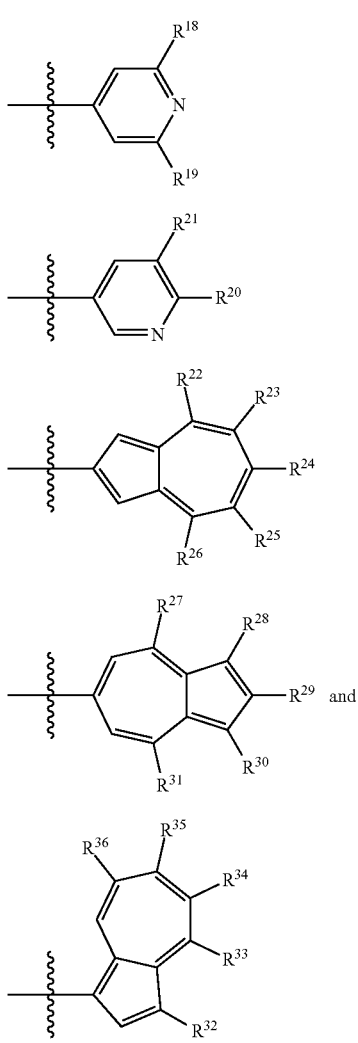

(II-5)
(II-6)
(II-7)
(II-8)
(II-9)

wherein:
R², R³, and R⁴, which are identical or different, represent a hydrogen, iodine or bromine atom, a nitro, linear $C_1$-$C_{12}$ alkyl, trifluoromethyl, di($C_1$-$C_4$)alkylamino, —C(O)($C_1$-$C_4$)alkyl or linear $C_1$-$C_4$ alkoxy radical;
R⁶, R⁸, R⁹, R¹⁰, R¹², R¹³, R¹⁴, R¹⁵ and R¹⁶, which are identical or different, represent a hydrogen or bromine atom, a linear $C_1$-$C_{12}$ alkyl or linear $C_1$-$C_4$ alkoxy radical, R⁹ and R¹⁰ together and/or R¹³ and R¹⁴ together and/or R¹⁵ and R¹⁶ together may also form an ethylenedioxy group (—O—(CH₂)₂—O—);
R⁷, R¹¹ and R¹⁷ represent a hydrogen, bromine or iodine atom, a nitro, linear $C_1$-$C_{12}$ alkyl, linear $C_1$-$C_4$ alkoxy, —CHO, —C(O)($C_1$-$C_4$)alkyl or —C(O)($C_1$-$C_4$) alkoxy radical or a thiophene ring optionally bearing one or more substituents chosen from Br, I, nitro, linear $C_1$-$C_{12}$ alkyl, linear $C_1$-$C_4$ alkoxy, —C(O)($C_1$-$C_4$)alkyl and —C(O)($C_1$-$C_4$)alkoxy;
R¹⁸ to R³⁶, which are identical or different, represent a hydrogen atom, a linear $C_1$-$C_4$ alkoxy radical, a nitro radical or a —C(O)($C_1$-$C_4$)alkoxy radical.

2. The method as claimed in claim 1, wherein n is equal to 1 or 2, and the R₁ radical(s) represent(s) a methyl radical.

3. The method claimed in claim 1, wherein the complexes of formulae (I-a) and (I-b) are chosen from:

[1,1',1'',1'''-(η4-1,3-cyclobutadiene-1,2,3,4-tetrayl)tetrakis[benzene]](η5-cyclopentadienyl)cobalt(I);
[1,1',1'',1'''-(η4-1,3-cyclobutadiene-1,2,3,4-tetrayl)tetrakis-4-n-butyl-benzene]](η5-cyclopentadienyl)cobalt (I);
[1,1',1'',1'''-(η4-1,3-cyclobutadiene-1,2,3,4-tetrayl)tetrakis[3,5-dimethoxy-benzene]](η5-cyclopentadienyl)cobalt(I);
[1,1'-[(1,2,3,4-η)-2,4-bis(4-methoxybenzene)-1,3-cyclobutadien-1,3-diyl]bis-[phenyl]](η5-2,4-cyclopentadien-yl)cobalt(I);
[1,1'-[(1,2,3,4-η)-2,4-bis(4-nitrobenzene)-1,3-cyclobutadien-1,3-diyl]bis[phenyl]](η5-2,4-cyclopentadien-yl)cobalt(I);
[1,1'-[(1,2,3,4-η)-2,4-bis(4-nitrobenzene)-1,3-cyclobutadien-1,3-diyl]bis[4-methoxybenzene]](η5-2,4-cyclopentadien-yl)cobalt(I);
[1,1'-[(1,2,3,4-η)-2,4-bis(4-bromobenzene)-1,3-cyclobutadien-1,3-diyl]bis[4-methoxybenzene]](η5-2,4-cyclopentadien-yl)cobalt(I);
[1,1',1'',1'''-(η4-1,3-cyclobutadiene-1,2,3,4-tetrayl)tetrakis[4-methyl benzoate]](η5-cyclopentadienyl)cobalt (I);
[1,1',1'',1'''-(η4-1,3-cyclobutadiene-1,2,3,4-tetrayl)tetrakis[2,2',5'-bithiophene]](η5-cyclopentadienyl)cobalt (I);
[1,1',1'',1'''-(η4-1,3-cyclobutadiene-1,2,3,4-tetrayl)tetrakis[2,2',5',2'',5''-terthiophene]](η5-cyclopentadienyl)cobalt(I);
[1,1',1'',1'''-(η4-cyclobutadiene-tetrakis 1,2,3,4-[2,5,2',5',2''-terthiophene-5''-carbaldehyde])]-(η5-cyclopentadienyl)cobalt(I);
[1,1',1'',1'''-(η4-cyclobutadiene-tetrakis 1,2,3,4-[2,5,2',5',2''-terthiophene-5''-bromo])](η5-cyclopentadienyl)cobalt(I);
-[1,1',1'',1'''-(η4-cyclobutadiene-tetrakis 1,2,3,4-[2,5,2',5',2''-terthiophene-5''-methoxy])](η5-cyclopentadienyl)cobalt(I);
[1,1',1'',1'''-(η4-cyclobutadiene-tetrakis 1,2,3,4-[2,5,2',5',2''-terthiophene-5''-nitro])](η5-cyclopentadienyl)cobalt(I);
[1,1',1'',1'''-(η4-cyclobutadiene-tetrakis 1,2,3,4-[2,5,2',5',2'-terthiophene-(4,4',4'')-trishexyl])](η5-cyclopentadienyl)cobalt(I);
[1,1',1'',1'''-(η4-cyclobutadiene-tetrakis 1,2,3,4-[2,5,2',5',2''-terthiophene-5''-dodecyl])](η5-cyclopentadienyl)cobalt(I);
[1,1',1'',1'''-(η4-cyclobutadiene-tetrakis 1,2,3,4-[2,5,2',5',2''-terthiophene-5''-iodo])](η5-cyclopentadienyl)cobalt (I);
[1,1',1'',1'''-(η4-cyclobutadiene-bis 1,3-[2,5,2',5',2''-terthiophene-5''-nitro], bis 2,4-[2,5,2',5',2''-terthiophene-5''-methoxy])](η5-cyclopentadienyl)-cobalt(I);
[1,1',1'',1'''-(η4-cyclobutadiene-bis 1,3-[2,5,2',5',2''-terthiophene-5''-bromo], bis 2,4-[2,5,2',5',2''-terthiophene-5''-methoxy])](η5-cyclopentadienyl)cobalt (I);
[1,1',1'',1'''-(η4-1,3-cyclobutadiene-1,2,3,4-tetrayl)tetrakis[2-thionyl]](η5-cyclopentadienyl)cobalt(I);
[1,1',1'',1'''-(η4-1,3-cyclobutadiene-1,2,3,4-tetrayl)tetrakis[3-pyridyl]](η5-cyclopentadienyl)cobalt(I);
[1,1',1'',1'''-(η4-1,3-cyclobutadiene-1,2,3,4-tetrayl)tetrakis[4-pyridyl]](η5-cyclopentadienyl)cobalt(I);
[1,1',1'',1'''-(η4-1,3-cyclobutadiene-1,2,3,4-tetrayl)tetrakis[1-azulenyl]](η5-cyclopentadienyl)cobalt(I);
[1,1',1'',1'''-(η4-1,3-cyclobutadiene-1,2,3,4-tetrayl)tetrakis[2-azulenyl]](η5-cyclopentadienyl)cobalt(I); and

[1,1',1'',1'''-(η4-1,3-cyclobutadiene-1,2,3,4-tetrayl)tetrakis[6-azulenyl]](η5-cyclopentadienyl)cobalt(1).

4. The method as claimed in claim 1, wherein the complexes of formulae (I-a) and (I-b) are chosen from:

[1,1',1'',1'''-(η4-1,3-cyclobutadiene-1,2,3,4-tetrayl)tetrakis[2,2',5'-bithiophene]](η5-cyclopentadienyl)cobalt(I);

[1,1',1'',1'''-(η4-1,3-cyclobutadiene-1,2,3,4-tetrayl)tetrakis[2,2',5'',2'',5''-terthiophene]](η5-cyclopentadienyl)cobalt(I);

[1,1',1'',1'''-(η4-cyclobutadiene-tetrakis 1,2,3,4-[2,5,2',5',2''-terthiophene-5''-carbaldehyde])](η5-cyclopentadienyl)cobalt(I);

[1,1',1'',1'''-(η4-cyclobutadiene-tetrakis 1,2,3,4-[2,5,2',5',2''-terthiophene-5''-bromo])](η5-cyclopentadienyl)cobalt(1);

1,1',1'',1'''-(η4-cyclobutadiene-tetrakis 1,2,3,4-[2,5,2',5',2''-terthiophene-5''-methoxy])](η5-cyclopentadienyl)cobalt(I);

[1,1',1'',1'''-(η4-cyclobutadiene-tetrakis 1,2,3,4-[2,5,2',5',2''-terthiophene-5''-nitro])](η5-cyclopentadienyl)cobalt(I);

[1,1',1'',1'''-(η4-cyclobutadiene-tetrakis 1,2,3,4-[2,5,2',5',2''-terthiophene-(4,4',4'')-trishexyl])](η5-cyclopentadienyl)cobalt(I);

[1,1',1'',1'''-(η4-cyclobutadiene-tetrakis 1,2,3,4-[2,5,2',5',2''-terthiophene-5''-dodecyl])](η5-cyclopentadienyl)cobalt(I);

[1,1',1'',1'''-(η4-cyclobutadiene-tetrakis 1,2,3,4-[2,5,2',5',2''-terthiophene-5''-iodo])](η5-cyclopentadienyl)cobalt(I);

[1,1',1'',1'''-(η4-cyclobutadiene-bis 1,3-[2,5,2',5',2''-terthiophene-5''-nitro], bis 2,4-[2,5,2',5',2''-terthiophene-5''-methoxy])](η5-cyclopentadienyl)cobalt(I); and

[1,1',1'',1'''-(η4-cyclobutadiene-bis 1,3-[2,5,2',5',2''-terthiophene-5''-bromo], bis 2,4-[2,5,2',5',2''-terthiophene-5''-methoxy])](η5-cyclopentadienyl)cobalt(I).

5. A photovoltaic conversion cell comprising:
at least one support;
a positive electrode;
an active layer having at least one electron donor and at least one electron acceptor; and
a negative electrode, wherein in said cell the electron donor is chosen from the compounds of formulae (I-a) and (I-b) as defined in claim 1.

6. The cell as claimed in claim 5, wherein the electron acceptor is selected from the group consisting of fullerene derivatives, carbon nanotubes, perylene derivatives and tetracyanoquinodimethane derivatives.

7. The cell as claimed in claim 6, wherein the electron acceptor is methyl [6,6]-phenyl-C61-butyrate.

8. The cell as claimed in claim 5, wherein the compound of formula (I-a) or (I-b)/electron acceptor weight ratio varies from 2/1 to 1/4.

9. The cell as claimed in claim 5, wherein the negative electrode is an aluminum electrode.

10. The cell as claimed in claim 5, wherein a buffer layer is inserted between the active layer and the positive electrode, said buffer layer consisting of a mixture of poly(3,4-ethylenedioxythiophene) and poly(sodium styrenesulfonate).

11. The cell as claimed in claim 5, wherein a buffer layer is inserted between the active layer and the negative electrode, said buffer layer consisting of a layer of lithium fluoride.

* * * * *